US007132408B2

(12) United States Patent
Boyer et al.

(10) Patent No.: US 7,132,408 B2
(45) Date of Patent: *Nov. 7, 2006

(54) COMPOSITION AND METHOD FOR INHIBITING PLATELET AGGREGATION

(75) Inventors: José L. Boyer, Chapel Hill, NC (US); James G. Douglass, III, Apex, NC (US); Sammy R. Shaver, Chapel Hill, NC (US); Krzysztof Bednarski, Raleigh, NC (US); Benjamin R. Yerxa, Raleigh, NC (US); Gillian M. Olins, San Diego, CA (US)

(73) Assignees: Inspire Pharmaceuticals, Inc., Durham, NC (US); University of North Carolina, Chapel Hill, NC (US)

( * ) Notice: Subject to any disclaimer, the term of this patent is extended or adjusted under 35 U.S.C. 154(b) by 290 days.

This patent is subject to a terminal disclaimer.

(21) Appl. No.: 10/814,007

(22) Filed: Mar. 30, 2004

(65) Prior Publication Data

US 2004/0220133 A1    Nov. 4, 2004

Related U.S. Application Data

(63) Continuation-in-part of application No. 09/934,970, filed on Aug. 21, 2001, which is a continuation-in-part of application No. 09/643,138, filed on Aug. 21, 2000.

(30) Foreign Application Priority Data

Aug. 20, 2001  (US) .................. PCT/US01/41818

(51) Int. Cl.
*A01N 43/04*     (2006.01)
*A61K 31/70*     (2006.01)
(52) U.S. Cl. ...................... 514/45; 514/43; 514/46; 514/47; 514/48
(58) Field of Classification Search ................ 514/43, 514/45, 46, 47, 48
See application file for complete search history.

(56) References Cited

U.S. PATENT DOCUMENTS

| | | | |
|---|---|---|---|
| 3,321,463 A | 5/1967 | Moffatt et al. ............ 260/211.5 |
| 4,330,550 A * | 5/1982 | Lautenschlager et al. ... 514/398 |
| 4,621,076 A | 11/1986 | Kuzuya et al. |
| 5,049,550 A | 9/1991 | Zamecnik ..................... 514/47 |
| 5,654,285 A | 8/1997 | Ingall et al. .................. 514/47 |
| 5,681,823 A | 10/1997 | Kim et al. ..................... 514/47 |
| 5,721,219 A | 2/1998 | Ingall et al. .................. 514/47 |
| 5,747,496 A | 5/1998 | Cox et al. .................... 514/258 |
| 5,814,609 A | 9/1998 | Markland, Jr. et al. ....... 514/12 |
| 5,837,861 A | 11/1998 | Pendergast et al. ......... 536/25.6 |
| 5,900,407 A | 5/1999 | Yerxa et al. ................... 514/47 |
| 5,955,447 A | 9/1999 | Ingall et al. ................... 514/47 |
| 6,166,022 A | 12/2000 | Brown et al. ................ 514/258 |
| 6,323,187 B1 | 11/2001 | Yerxa et al. .................. 514/51 |
| 6,348,589 B1 | 2/2002 | Pendergast et al. ........ 536/25.6 |
| 6,596,725 B1 | 7/2003 | Peterson et al. ........... 514/25.6 |

FOREIGN PATENT DOCUMENTS

| | | |
|---|---|---|
| GB | 1407903 | 10/1975 |
| WO | WO 89/04321 | 5/1989 |
| WO | WO 92/01673 | 2/1992 |
| WO | WO 92/17488 | 10/1992 |
| WO | WO 94/08593 | 4/1994 |
| WO | WO 94/18216 | 8/1994 |
| WO | WO 97/03084 | 1/1997 |
| WO | WO 97/29456 | 8/1997 |
| WO | WO 98/03182 | 1/1998 |
| WO | WO 98/28300 | 7/1998 |
| WO | WO 98/34593 | 8/1998 |
| WO | WO 99/01138 | 1/1999 |
| WO | WO 99/32085 | 7/1999 |
| WO | WO 99/61012 | 12/1999 |
| WO | WO 00/33080 | 6/2000 |
| WO | WO 00/34283 | 6/2000 |
| WO | WO 00/39145 | 7/2000 |
| WO | WO 00/50024 | 8/2000 |
| WO | WO 01/19826 | 3/2001 |
| WO | WO 01/36421 | 5/2001 |
| WO | WO 01/39781 | 6/2001 |
| WO | WO 02/16381 A2 | 2/2002 |

OTHER PUBLICATIONS

Moffatt, et al., "Nucleoside polyphosphates . . . ", Journal of the American Chemical Society (1958), 80, 3756-61.

(Continued)

*Primary Examiner*—Patrick Lewis
(74) *Attorney, Agent, or Firm*—Howrey LLP; Viola T. Kung

(57) ABSTRACT

This invention is directed to a method of preventing or treating diseases or conditions associated with platelet aggregation. The method is also directed to a method of treating thrombosis. The method comprises administering to a subject a pharmaceutical composition comprising a therapeutic effective amount of $P2Y_{12}$ receptor antagonist compound, wherein said amount is effective to bind the $P2Y_{12}$ receptors on platelets and inhibit ADP-induced platelet aggregation. The $P2Y_{12}$ receptor antagonist compounds useful for this invention include mononucleoside 5'-monophosphates, mononucleoside polyphosphates, and dinucleoside polyphosphates of general Formula I, or salts thereof. The present invention also provides novel compounds of mononucleoside 5'-monophosphates, mononucleoside polyphosphates, and dinucleoside polyphosphates. The present invention further provides pharmaceutical formulations comprising mononucleoside 5'-monophosphates, mononucleoside polyphosphates, or dinucleoside polyphosphates.

27 Claims, 11 Drawing Sheets

OTHER PUBLICATIONS

International Search Report PCT/US01/41818, Mar. 11, 2002, PCT.

Hamilton, A. et al., "Design of Substrate-Site-Directed Inhibitors of Adenylate Kinase and Hexokinase. Effect of Substrate Substituents on Affinity for the Adenine Nucleotide Sites", *J. Med. Chem.*, 19:1371-1377 (1976).

Hiratsuka T., "Affinity Labeling of the Myosin ATPase with Riobse-Modified Fluroescent Nucleotides and Vanadate", *J. Biochem.*, 96:147-154 (1984).

Martin, P. et al., "Structure-Activity Studies of Analogs of $\beta,\gamma$-Methylene-ATP at $P_{2x}$-Purinoceptors in the Rabbit Ear Central Artery", *Drug Development Research*, 36: 153-165 (1995).

Metzker, M. et al., "Termination of DNA synthesis by novel 3'-modified-deoxyribonucleoside 5'-triphophate", *Nucleic Acids Research*, 22:4259-4267 (1994).

Pelicano, H. et al., "Study of the substrate-binding properties of bovine liver adenosine kinase and inhibition by fluorescent nucleoside analogues", *Eur. J. Biochem.*, 248:930-937 (1997).

Richard, J. and Frey, P.A., "Stereochemical Course of Thiophosphoryl Group Transfer Catalyzed by Adenylate Kinase", *J. Am. Chem. Soc.*, 100:7757-7758 (1978).

Sekine, M. et al., "New Type of Chemical Oxidative Phosphorylation: Activation of Phosphonate Function by Use of Triisoprobylbenzenesulfonyl Chloride", *Tetrahedron Letters*, 1145-1148 (1997).

Zatorski, A. et al., "Chemical Synthesis of Benzamide Adenine Dinucleotide: Inhibition of Inosine Monophosphate Dehydrogenase (Types I and II)", *Journal of Medicinal Chemistry, American Chemical Society*, 39:2422-2426 (1996).

Alessi, D. et al., "Synthesis and Properties of a Conformationally Restricted Spin-Labeled Analog of ATP and Its Interaction with Myosin and Skeletal Muscle" *Biochemistry* (1992), 31(34), 8043-54.

Antiplatelet Trialists'Collaberation., "Collaborative overview of randomised trials of antiplatelet therapy-I : Prevention of Death, myocardial infarction, and stroke by prolonged antiplatelet therapy in various categories of patients," *Br. Med. J.* 308: 81-106 (1994).

Antiplatelet Trialists'Collaberation., "Collaborative overview of randimised trials of antiplatelet therapy-II : maintenance of Vascular graft or arterial patency by antiplatelet therapy," *Br. Med. J.* 308: 159-168 (1994).

Antman, E, for The TIMI 9a investigators, "Hirudin in Acute Myocardial Infarction," , *Circulation*, 90(4):1624-1630 (1994).

Bernat, A., et al., "Effect of Various Antiplatelet Agents on Acute Arterial Thrombosis in the Rat," *Thromb. Haemostas.* (1993) 70(5):812-816.

Bujalowski, W. et al., "Structural Characteristics of the Nucleotide-Binding Site of *Escherichia coli* Primary Replicative Helicase DnaB Protein. Studies with Ribose and Base-Modified Fluorescent Nucleotide Analogs" *Biochemistry* (1994), 33(15), 4682-94.

Bush, L., et al., "Effects of the selective thromboxane synthetase inhibitor dazoxiben on variations in cyclic blood flow in stenosed canie coronary arteries," Circulation 69(6):1161-1170, (1984).

Cardullo, R. A. et al., "Synthesis, Purification, and Characterization of 2,4,6-Trinitrophenyl-UDP-galactose: A Fluorescent Substrate for Galactosyltransferase" *Analytical Biochemistry* (1990), 188(2), 305-9.

Carvalho-Alves, P. et al., "Stoichiometric Photlabeling of Two Distinct Low and High Affinity Nucleotide Sites in Sarcoplasmic Reticulum ATPase" *Journal of Biological Chemistry* (1985), 260(7), 4282-7.

Chapal, J. et al., "Comparitive effects of adenosine-5'-triphosphate and related analogs on insulin secretion from the rat pancreas" *Fundamental & Clinical Pharmacology* (1997), 11(6), 537-545.

Folts, J. et al., "Platelet Aggregation in Partially Obstructed Vessels and its Elimination with Asprian," Circulation 54(3):365-370 (1976).

Frederick, L.G., et al., "The Protective Dose of the Potent GPIIb/IIIa Antagonist SC-54701A is Reduced When Used in Combination with Asprian and Heparin in a Canie Model of Coronary Artery Thrombosis," Circulation 93(1):129-134 (1996).

Geiger, J., et al., "Specific Impairment of Human Platelet P2Y ac ADP Receptor-Mediated Signaling by the Antiplatelet Drug Clopidogrel," *Aterioscler. Thromb. Vasc. Biol.* 19:2007-2011 (1999).

Hass, W., et al., "A Randomized Trial Comparing Ticlopidine Hydrochloride with Asprian for the Prevention of Stroke for High-Risk Patients," *N. Engl. J. Med.*, 321(8):501-507 (1989).

Herbert, J.M. et al., Inhibitory Effect of Clopidogrel on Platelet Adhesion and Intimal Proliferation After Arterial Injury in Rabbits, *Arterioscl. Thromb.* (1993) 13(8):1171-1179.

Hiratsuka, Toshiaki, "Biological Activities and Spectroscopic Properties of Chromophoric and Fluorescent Analogs of Adenine Nucleoside and Nucleotides, 2',3'-O-(2,4,6-Trinitrocyclohexadienylidene) Adenosine Derivatives" *Biochemicha et Biophysica Acta* (1982), 719(3), 509-17.

Hiratsuka, Toshiaki "Monitoring the Myosin ATPase Reaction Using a Sensitive Fluorescent Probe: Pyrene-Labeled ATP" *Biophysical Journal* (1997), 72(2, Pt. 1), 843-849.

Hourani, et al., The Platelet ADP Receptors Meeting, La Thuile, Italy, Mar. 29-31, 2000.

Humphries, R.G., et al., "Pharmacological profile of the novel P2T-Purinoceptor antagonist, FPL 67085 in vitro and in the anaestheized rat in vitro," Br. J. Pharmacol. 115:1110-1116 (1995).

Ikehara, M. et al., "III. Interaction Between Synthetic Adenosine Triphosphate Analogs and Actomyosin Systems" *Biochimica et Biophysica Acta* (1965), 100(2), 471-8.

Ikehara, M. et al., "Unusual Rapid Cleavage of Terminal Phosphate Group of N6-Disubstituted Adenosine 5'-Triphosphate (ATP)by Divalent Cation" *Biochimica et Biophysica Acta* (1964), 85(3), 512-515.

Ingall, A., et al. , "Antagonists of the Platelet P2t Receptor: A Novel Approach to Antithrombotic Therapy," *J. Med. Chem.* 42: 213-220 (1999).

Kim, et al., "Characterization of the Purinergic $P_2$ Receptors in PC12 Cells," *Journal of Biological Chemistry* (1994), 269:6471-6477.

Kwiatkowski, A. et al., "Mapping of the Adenosine 5'-Triphosphate Binding Site of Type II Calmodulin-Dependent Protein Kinase" *Biochemistry* (1987), 26(24), 7636-40.

Lazarowski, E., et al., "Pharmacological selectivity of the cloned human P2u-purinoceptor: potent activation by diadenosine tetraphosphate," *Brit. J. Pharm.* 116:1619-1627 (1995).

Lekstrom, J and William R. Bell, "Asprian in the Prevention of Thrombosis," *Medicine* 70(3):161-178 (1991).

Lowe, G. et al., "Evidence of a Dissociative $S_N1(P)$ Mechanism of Phosphoryl Transfer by Rabbit Muscle Pyruvate Kinase" *Journal of the Chemical Society, Perkin Transactions 1: Organic and Bio-Organic Chemistry* (1972-1999) (1978), (12), 1622-30.

Marlan, M., "Acetyl Derivatives of Nucleoside 5'-Triphosphates. I." *Microchemical Journal* (1984), 29(2), 219-27.

Mayer, I. et al., "Interaction of Fluorescent Adenine Nucleotide Derivatives with ADP/ATP Carrier in Mitochondria. 1. Comparison of Various 3'-O-Ester Adenine Nucleotide Derivatives" *Biochemistry* (1984), 23(11), 2436-42.

Mickelson, J.K., et al., "Antiplatelet Antibody [7E3 F(ab')2] Prevents Rethrombosis After Recombinant Tissue-Type Plasminogen Activator-Induced Coronary Artery Thrombolysis in a Canie Model," Circulation 81(2):617-627 (1990).

Murataliev, M. et al., "Interaction of mitochondrial $F_1$-ATPase with trinitrophenyl derivatives of ATP. Photoaffinity labeling of binding sites with 2-azido-2',3'-O-(2,4,6-trinitrophenyl)adenosine 5'-triphosphate" *European Journal of Biochemistry* (1995), 232(2), 578-85.

Neuhaus., K. L. et al., "Safety Observations from the Piolet Phase of the Randomized r-Hirudin for Improvement of Thrombolysis (HIT-III) Study," Circulation, 90(4): 1638-1642 (1994).

Oliveira, C. R. G. et al., "Interaction of Spin-Labeled Nucleotides with Sarcoplasmic Reticulum Adenosinetriphosphatase" *Biochemistry* (1988), 27(16), 5923-7.

Olivier, K., et al., "Acute Safety and Effects on Mucociliary Clearance of Aerosolized Uridine 5'—Triphosphate +Amiloride in Normal Human Adults,"—*Am. J. Respir. Crit. Care Med.* 154:217-223 (1996).

Quinn, M and Desmond J. Fitzgerald, "Ticlopidine and Clopidogrel," *Circulation* 100(15):1667-1672 (1999).

Ray, S. et al., "Microenvironment at the Substrate Binding Subsite of the Active Site of UDPglucose 4-Epimerase from Kluyveromyces Fragilis Using a Fluroescent Analog of UMP" *Indian Journal of Biochemistry & Biophysics* (1992), 29(2), 209-13.

Romson, J., et al, "Electrical Induction of Coronary Artery Thrombosis in the Ambulatory Canine: A model for IN VIVO Evaluation of Anti-Thrombotic Agents," Thromb. Res. 17:841-853 (1980).

Seebregts, C. et al., "2',3'-O-(2,4,6-Trinitrophenyl)-8-Azido-adenosine Mono-, Di-, and Triphosphates as Photoaffinity Probes of the $Ca^{2+}$-ATPase of Sarcoplasmic Reticulum. Regulatory/Superfluorescent Nucleotides Label the Catalytic Site with High Efficiency" *Journal of Biological Chemistry* (1989), 264(4), 2043-52.

Shebuski, R., et al., "Acceleration of Recombinant Tissue-Type Plasminogen Activator-Induced Thrombolysis and Prevention of Reocclusin by the Combination of Heparin and the Arg-Gly-Asp-Containing Peptide Bitistatin in a Canie Model of Coronary Thrombosis," Circulation 82(1):169-177 (1990).

Soslau, G. et al., "Aggregation of Human and Canine Platelets: Modulation by Purine Nucleotides" *Thrombosis Research* (1993), 72(2), 127-37.

Thoenges D. et al., "Tight Binding of Bulky Fluorescent Derivatives of Adenosine to the Low Affinity $E_2$ATP Site Leads to Inhibition of Na+/K+-ATPase. Analysis of Structural Requirements of Fluorescent ATP Derivatives with a Koshland-Nemethy-Filmer Model of Two Interacting ATP Sites" *Journal of Biological Chemistry* (Jan. 22, 1999), 274(4), 1971-8.

Tschopp, J.F., et al., "Inhibition of coronary artery reocclusion after thrombolysis with an RGD-containing peptide with no significant effect on bleeding time," Coron. Artery Dis. 4:809-817(1993).

Vigne, P. et al., "Benzoyl ATP Is an Antagonist of Rat and Human $P2Y_1$ Receptors and of Platelet Aggregation" *Biochemical and Biophysical Research Communications* (1999), 256(1), 94-97.

Ward, D. et al., "Photoinactivation of Fluorescein Isothiocyanate-modified Na,K-ATPase by 2'(3')-O-2,4,6-Trinitrophenyl)8-azidoadenosine 5'-Diphosphate. Abolition of E1 and E2 Partial Reactions by Sequential Block of High and Low Affinity Nucleotide Sites" *Journal of Biological Chemistry* (1998), 273(23), 14277-14284.

Weber, M., et al., "Low-Dose Asprian Verses Anticoagulants for Prevention of Coronary Graft Occlusion," *Am. J. Cardiol.* 66:1461-1468 (1990).

* cited by examiner

| Structure | Name | ADP-induced aggregation (%) | IC$_{50}$ (uM) |
|---|---|---|---|
| 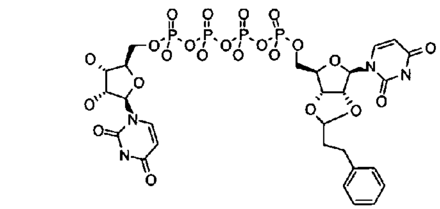 | 2',3' phenylpropionaldehyde acetal Up4U | | |
| 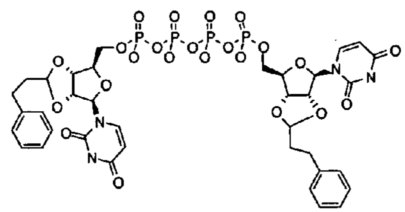 | di 2',3' phenylpropionaldehyde acetal Up4U | | |
| 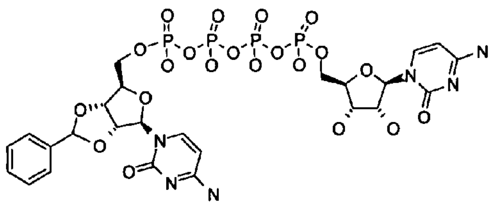 | 2',3' benzaldehyde acetal Cp4C | | |
| 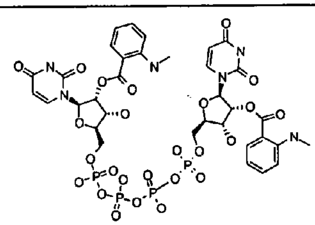 | Bis MANT Up4U | | 9 |

COMPOSITION AND METHOD FOR INHIBITING PLATELET AGGREGATION

This application is a continuation-in-part of U.S. application Ser. No. 09/934,970, filed Aug. 21, 2001, which is a continuation-in-part of U.S. application Ser. No. 09/643,138, filed Aug. 21, 2000. The contents of both applications are incorporated herein by reference in their entirety. The application also claims foreign priority benefit under 35 U.S.C. 365(a) of PCT application PCT/US01/41818, filed Aug. 20, 2001, which designated at least one country other than the United States.

TECHNICAL FIELD

This invention relates to mono- and dinucleoside polyphosphate compounds and the method of using such compounds in the prevention or treatment of diseases or conditions associated with platelet aggregation, including thrombosis in humans and other mammals.

BACKGROUND OF THE INVENTION

Hemostasis is the spontaneous process of stopping bleeding from damaged blood vessels. Precapillary vessels contract immediately when cut; within seconds, thrombocytes, or blood platelets, are bound to the exposed matrix of the injured vessel by a process called platelet adhesion. Platelets also stick to each other in a phenomenon known as platelet aggregation to form a platelet plug to stop bleeding quickly.

An intravascular thrombus results from a pathological disturbance of hemostasis. Platelet adhesion and aggregation are critical events in intravascular thrombosis. Activated under conditions of turbulent blood flow in diseased vessels or by the release of mediators from other circulating cells and damaged endothelial cells lining the vessel, platelets accumulate at a site of vessel injury and recruit further platelets into the developing thrombus. The thrombus can grow to sufficient size to block off arterial blood vessels. Thrombi can also form in areas of stasis or slow blood flow in veins. Venous thrombi can easily detach portions of themselves called emboli that travel through the circulatory system and can result in blockade of other vessels, such as pulmonary arteries. Thus, arterial thrombi cause serious disease by local blockade, whereas venous thrombi do so primarily by distant blockade, or embolization. These conditions include venous thrombosis, thrombophlebitis, arterial embolism, coronary and cerebral arterial thrombosis, unstable angina, myocardial infarction, stroke, cerebral embolism, kidney embolisms and pulmonary embolisms.

A number of converging pathways lead to platelet aggregation. Whatever the initial stimulus, the final common event is crosslinking of platelets by binding fibrinogen to a membrane binding site, glycoprotein IIb/IIIa (GPIIb/IIIa). Compounds that are antagonists for GPIIb/IIIa receptor complex have been shown to inhibit platelet aggregation (U.S. Pat. Nos. 6,037,343 and 6,040,317). Antibodies against GPIIb/IIIa have also been shown to have high antiplatelet efficacy (The EPIC investigators, *New Engl. J. Med.* (1994) 330:956–961). However, this class of antiplatelet agents sometimes causes bleeding problems.

Thrombin can produce platelet aggregation largely independently of other pathways but substantial quantities of thrombin are unlikely to be present without prior activation of platelets by other mechanisms. Thrombin inhibitors such as hirudin are highly effective antithrombotic agents. However, functioning as both antiplatelet and anti-coagulant agents, thrombin inhibitors again can produce excessive bleeding. (The TIMI 9a investigators, The GUSTO IIa investigators, Circulation, 90: 1624–1630 (1994); *Circulation*, 90: 1631–1637 (1994); Neuhaus K. L. et al., *Circulation*, 90: 1638–1642 (1994))

Various antiplatelet agents have been studied for many years as potential targets for inhibiting thrombus formation. Some agents such as aspirin and dipyridamole have come into use as prophylactic antithrombotic agents, and others have been the subjects of clinical investigations. To date, the powerful agents such as disintegrins, and the thienopyridines ticlopidine and clopidogrel have been shown to have substantial side effects, while agents such as aspirin have useful but limited effectiveness (Hass, et al., *N. Engl. J. Med.*, 321:501–507 (1989); Weber, et al., *Am. J. Cardiol.* 66:1461–1468 (1990); Lekstrom and Bell, *Medicine* 70:161–177 (1991)). In particular, use of the thienopyridines in antiplatelet therapy has been shown to increase the incidence of potentially life threatening thrombotic thrombocytopenic purpura (Bennett, C. L. et al *N. Engl. J. Med,* (2000) 342: 1771–1777). Aspirin, which has a beneficial effect on platelet aggregation (*Br. Med. J.* (1994) 308: 81–106; 159–168), acts by inducing blockade of prostaglandin synthesis. Aspirin has no effect on ADP-induced platelet aggregation, and thus has limited effectiveness on platelet aggregation. Furthermore, its well documented high incidence of gastric side effects limits its usefulness in many patients. Clinical efficacy of some newer drugs, such as ReoPro (7E3), is impressive, but recent trials have found that these approaches are associated with an increased risk of major bleeding, sometimes necessitating blood transfusion (*New Engl. J. Med.* (1994) 330:956–961). Thus it appears that the ideal "benefit/risk" ratio has not been achieved.

Recent studies have suggested that adenosine 5'-diphosphate (ADP), a common agonist, plays a key role in the initiation and progression of arterial thrombus formation (Bernat, et al., *Thromb. Haemostas.* (1993) 70:812–826); Maffrand, et al., *Thromb. Haemostas.* (1988) 59:225–230; Herbert, et al., *Arterioscl. Thromb.* (1993) 13:1171–1179). ADP induces platelet aggregation, shape change, secretion, influx and intracellular mobilization of $Ca^{+2}$, and inhibition of adenylyl cyclase. Binding of ADP to platelet receptors is required for elicitation of the ADP-induced platelet responses. There are at least three P2 receptors expressed in human platelets: a cation channel receptor $P2X_1$, a G protein-coupled receptor $P2Y_1$, and a G protein-coupled receptor $P2Y_{12}$ (also referred to as $P^2Y_{ac}$ and $P2_T$). The $P2X_1$ receptor is responsible for rapid calcium influx and is activated by ATP and by ADP. However, its direct role in the process of platelet aggregation is unclear. The $P2Y_1$ receptor is responsible for calcium mobilization, shape change and the initiation of aggregation. $P2Y_{12}$ receptor is responsible for inhibition of adenylyl cyclase and is required for full aggregation. (Hourani, et al., The Platelet ADP Receptors Meeting, La Thuile, Italy, Mar. 29–31, 2000)

Ingall et al. (*J. Med. Chem.* 42: 213–220, (1999)) describe a dose-related inhibition of ADP-induced platelet aggregation by analogues of adenosine triphosphate (ATP), which is a weak, nonselective but competitive $P2Y_{12}$ receptor antagonist. Zamecnik (U.S. Pat. No. 5,049,550) discloses a method for inhibiting platelet aggregation in a mammal by administering to said mammal a diadenosine tetraphosphate compound of App(CH$_2$)ppA or its analogs. Kim et al. (U.S. Pat. No. 5,681,823) disclose $P^1$, $P^4$-dithio-$P^2$, $P^3$-monochloromethylene 5', 5'''diadenosine $P^1$, $P^4$-tetraphosphate as an antithrombotic agent. The thienopyridines ticlopidine and clopidogrel, which are metabolized to antagonists of the platelet P2Y$_{12}$ receptor, are shown to inhibit platelet function in vivo (Quinn and Fitzgerald, *Circulation* 100:1667–1672 (1999); Geiger, et al., *Arterioscler. Thromb. Vasc. Biol.* 19:2007–2011 (1999)).

There is a need in the area of cardiovascular and cerebrovascular therapeutics for an agent that can be used in the prevention and treatment of thrombi, with minimal side effects, such as unwanted prolongation of bleeding, while preventing or treating target thrombi.

SUMMARY OF THE INVENTION

This invention is directed to a method of preventing or treating diseases or conditions associated with platelet aggregation; such diseases include venous thrombosis, thrombophlebitis, arterial embolism, coronary and cerebral arterial thrombosis, unstable angina, myocardial infarction, stroke, cerebral embolism, kidney embolisms and pulmonary embolisms. The method is also directed to a method of preventing, treating or reducing the incidence of: thrombosis, thrombotic events, embolic events or pathological conditions associated with such events, where the thrombosis, thrombotic event or embolic event occurs during or after surgery.

The method comprises administering to a subject a pharmaceutical composition comprising a therapeutic effective amount of P2Y$_{12}$ receptor antagonist compound, wherein said amount is effective to bind the P2Y$_{12}$ receptors on platelets and inhibit ADP-induced platelet aggregation.

The P2Y$_{12}$ receptor antagonist compounds useful for this invention include compounds of general Formula I, or salts thereof:

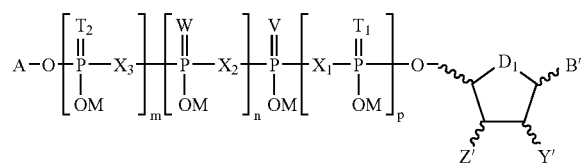

Formula I wherein:

$X_1$, $X_2$, and $X_3$ are independently oxygen, methylene, monochloromethylene, dichloromethylene, monofluoromethylene, difluoromethylene, or imido;

$T_1$, $T_2$, W, and V are independently oxygen or sulfur;

m=0, 1 or 2;

n=0 or 1;

p=0,1, or 2;

where the sum of m+n+p is from 0 to 5; (monophosphate to hexaphosphate) M=H or a pharmaceutically-acceptable inorganic or organic counterion;

$D_1$=O or $CH_2$;

B' is a purine or a pyrimidine residue according to general Formulae IV and V which is linked to the 1' position of the furanose or carbocycle via the 9- or 1-position of the base, respectively;

Y'=H, OH, or $OR_1$;

Z'=H, OH, or $OR_2$;

with the proviso that when A=M, at least one of Y' and Z' is equal to $OR_1$ or $OR_2$ respectively;

A=M, or

A is a nucleoside residue which is defined as:

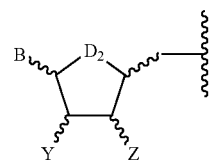

and which is linked to the phosphate chain via the 5' position of the furanose or carbocycle;

wherein:

$D_2$=O or $CH_2$;

Z=H, OH, or $OR_3$;

Y=H, OH, or $OR_4$;

with the proviso that at least one of Y', Z', Y and Z is equal to $OR_1$, $OR_2$, $OR_3$ or $OR_4$ respectively;

B is a purine or a pyrimidine residue according to general Formulae IV and V which is linked to the 1'-position of the furanose or carbocycle via the 9- or 1'-position of the base, respectively;

$R_1$, $R_2$, $R_3$, and/or $R_4$ are residues which are linked directly to the 2'- and/or 3'-hydroxyls of the respective furanose or carbocycle via a carbon atom according to Formula II, or linked directly to two (2'- and 3'-)hydroxyls of the respective furanose or carbocycle via a common carbon atom according to Formula II, such that from one to four independent residues of $R_1$, $R_2$, $R_3$ and $R_4$ falling within the definition of Formula III are present or from one to two independent residues made up of R+$R_2$ and/or $R_3$+$R_4$ are present.

The present invention also provides novel mononucleoside 5'-monophosphate-, mononucleoside polyphosphate-, and dinucleoside polyphosphate-compounds which are useful in this invention. The present invention further provides pharmaceutical formulations comprising mononucleoside 5'-monophosphates, mononucleoside polyphosphates, or dinucleoside polyphosphates.

DETAILED DESCRIPTION OF THE INVENTION

Figure 1:
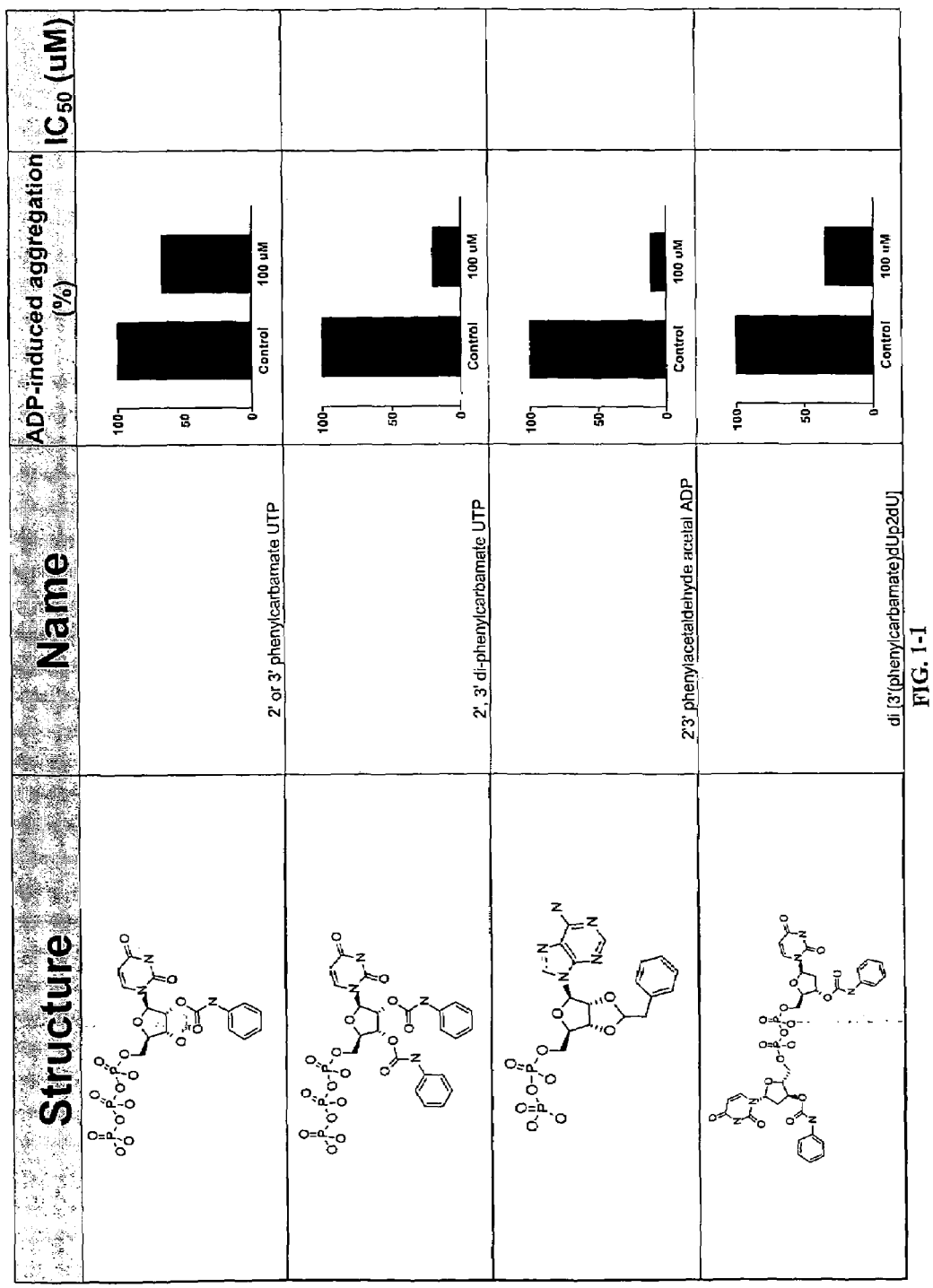
FIGS. 1-1 to 1-11 to show the effect of inhibition of ADP-induced aggregation by different compounds.
Figures 1, 2:
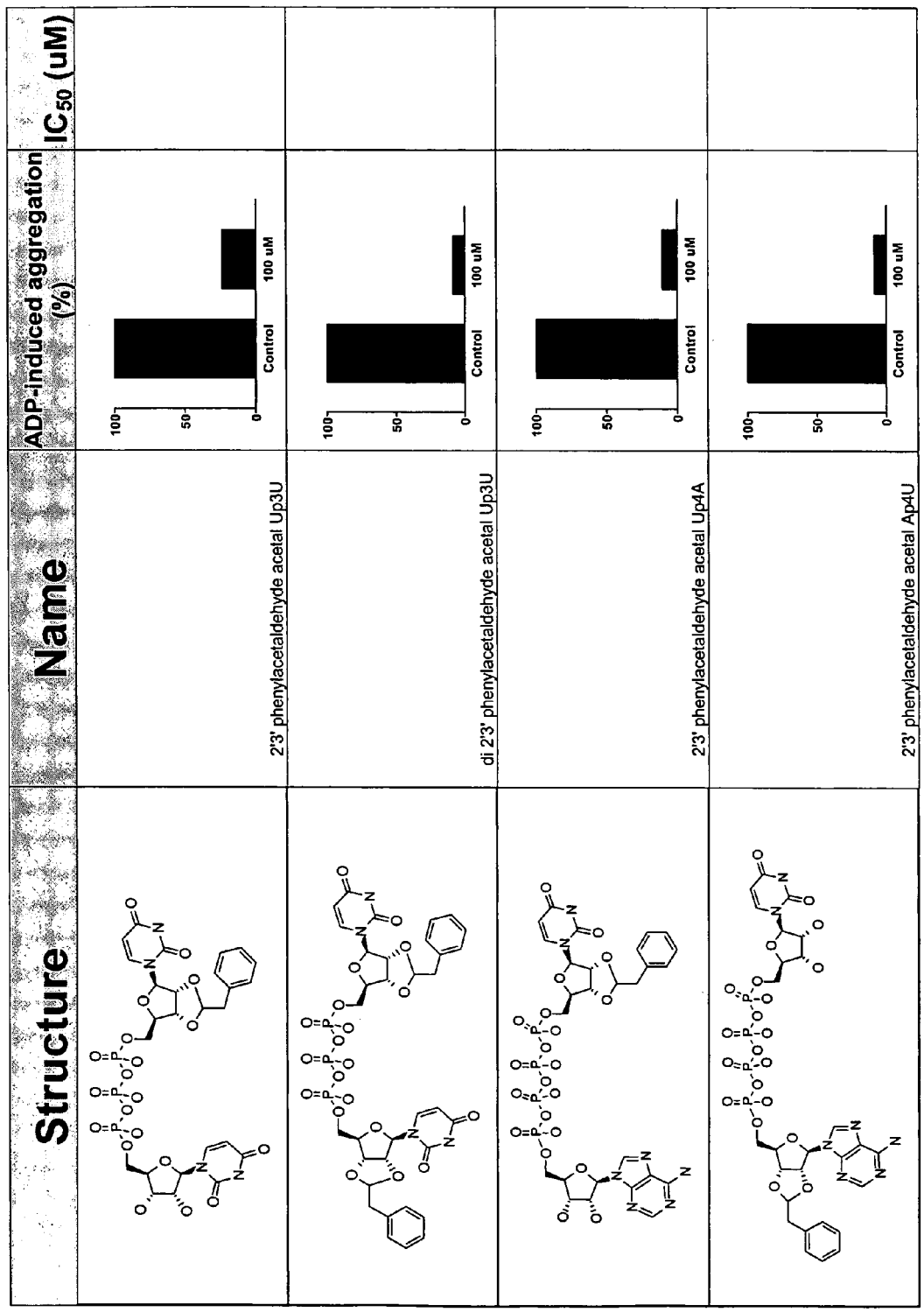
Figures 1, 2, 3:
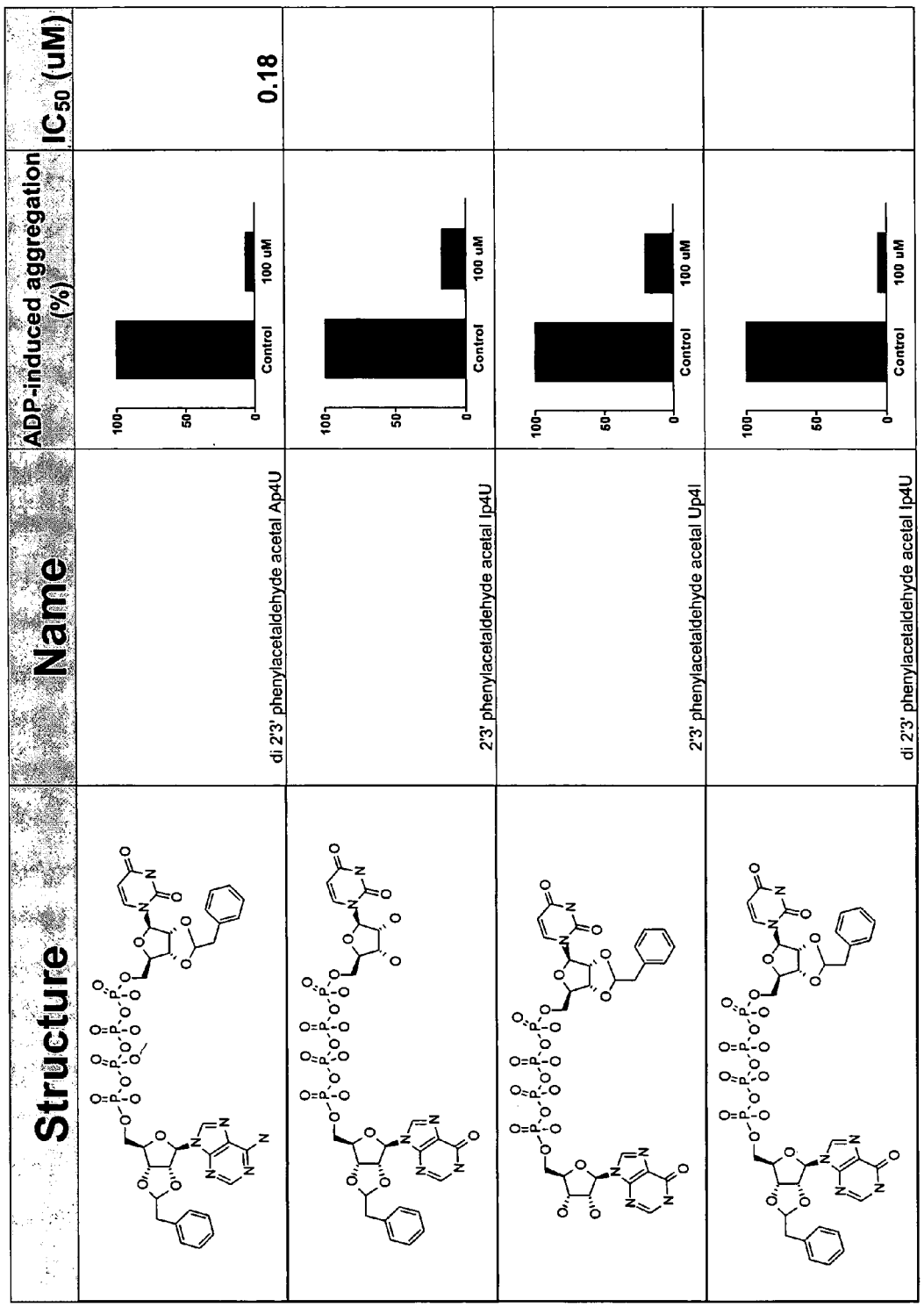
Figures 1, 2, 3, 4:
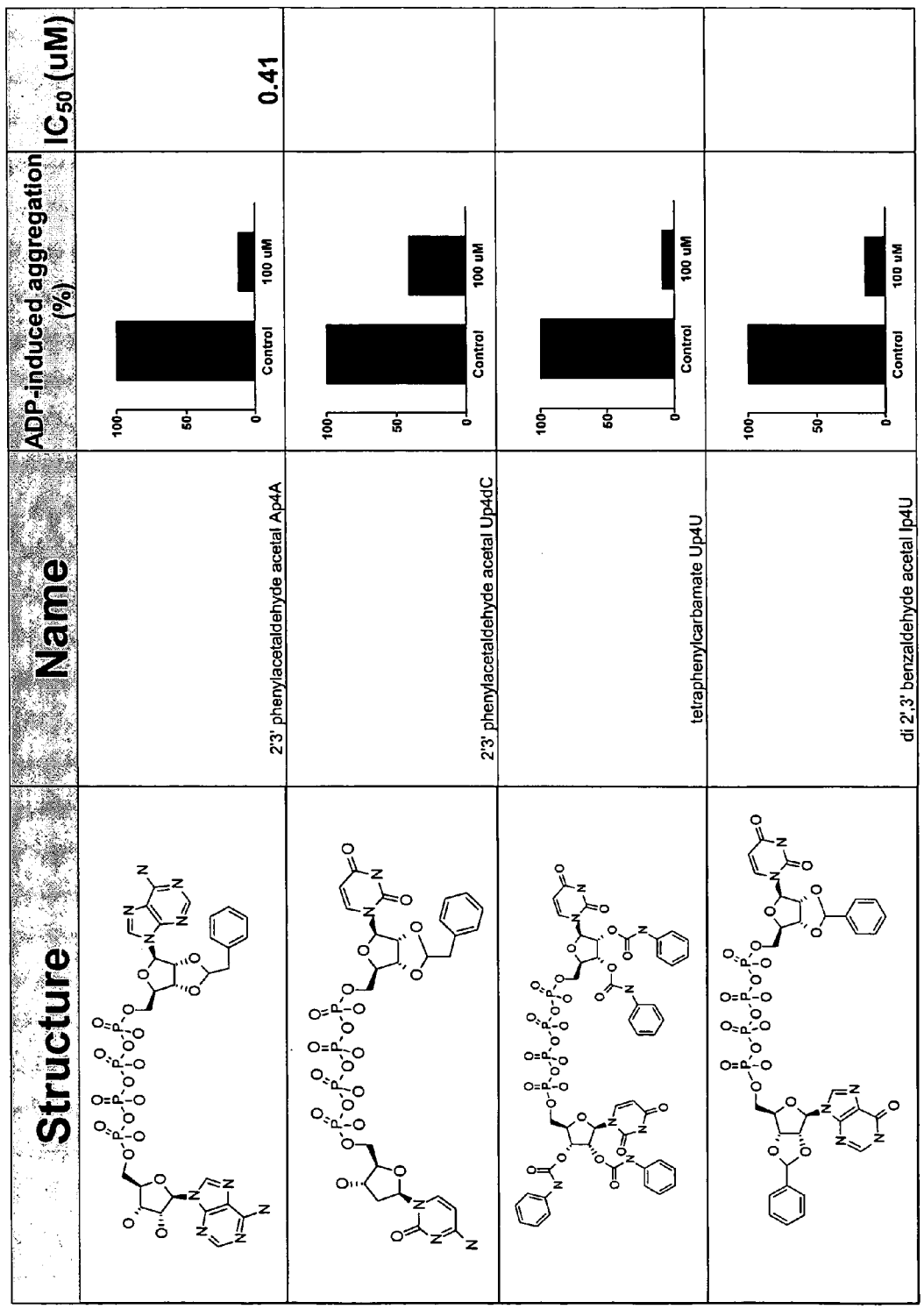
Figures 1, 2, 3, 4, 5:
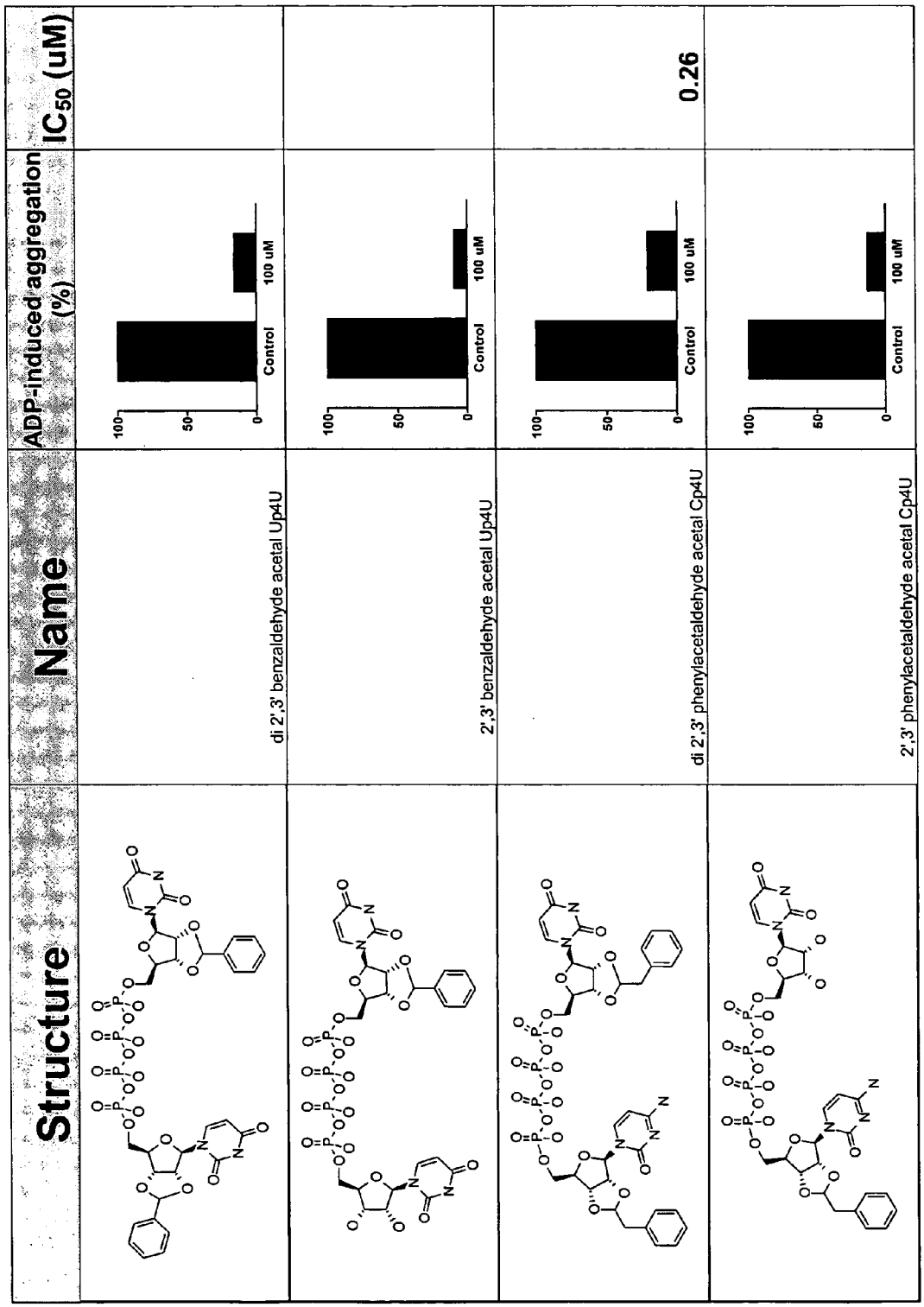
Figures 1, 2, 3, 4, 5, 6:
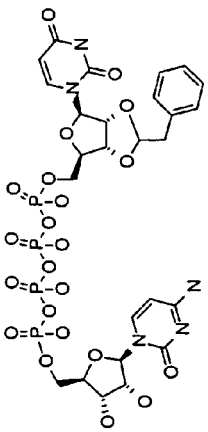
Figures 1, 2, 3, 4, 5, 6, 7:
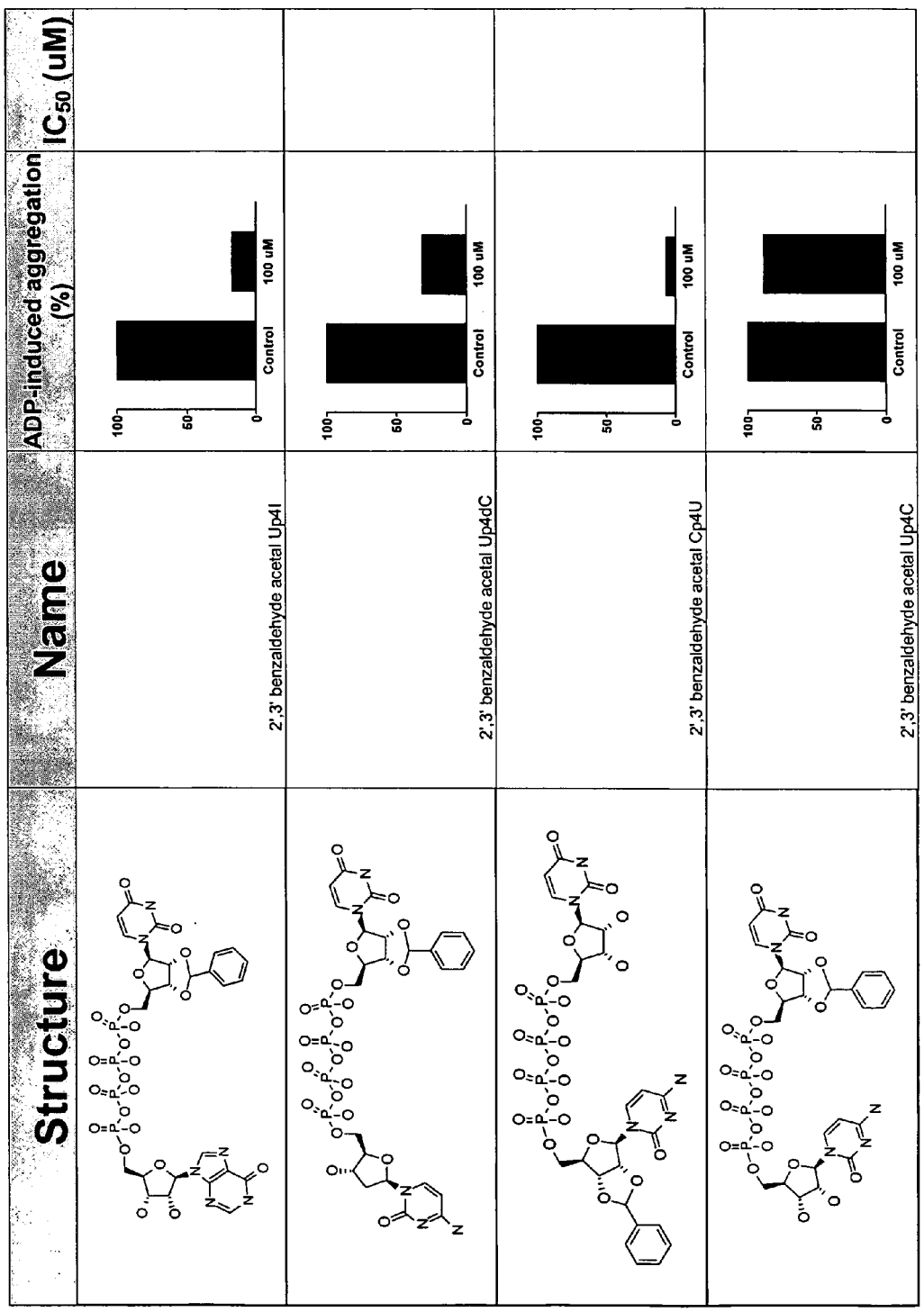
Figures 1, 2, 3, 4, 5, 6, 7, 8:
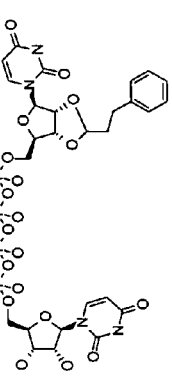
Figures 1, 2, 3, 4, 5, 6, 7, 8, 9:
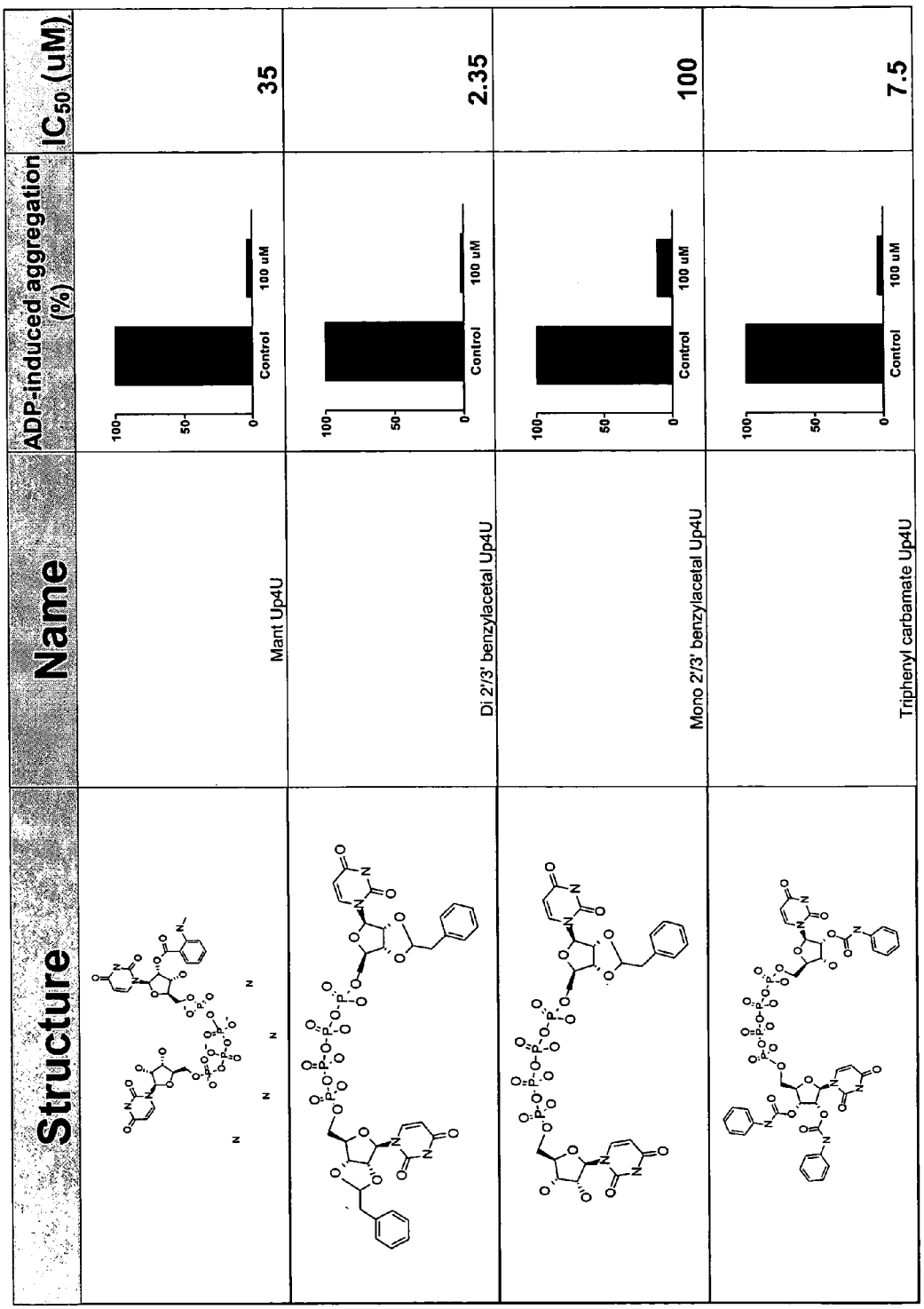
Figures 1, 2, 3, 4, 5, 6, 7, 8, 9, 10:
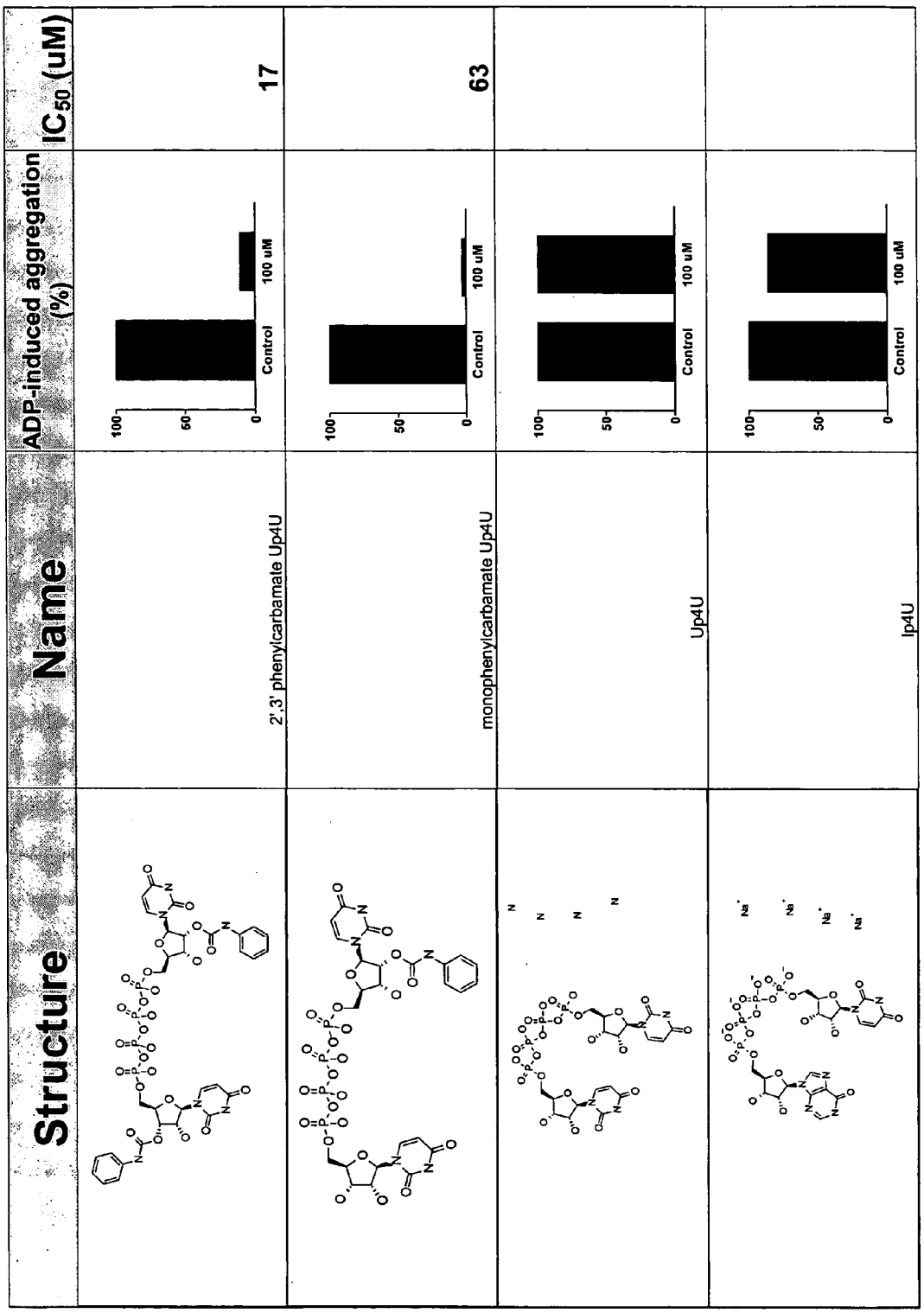
Figures 1, 2, 3, 4, 5, 6, 7, 8, 9, 10, 11:
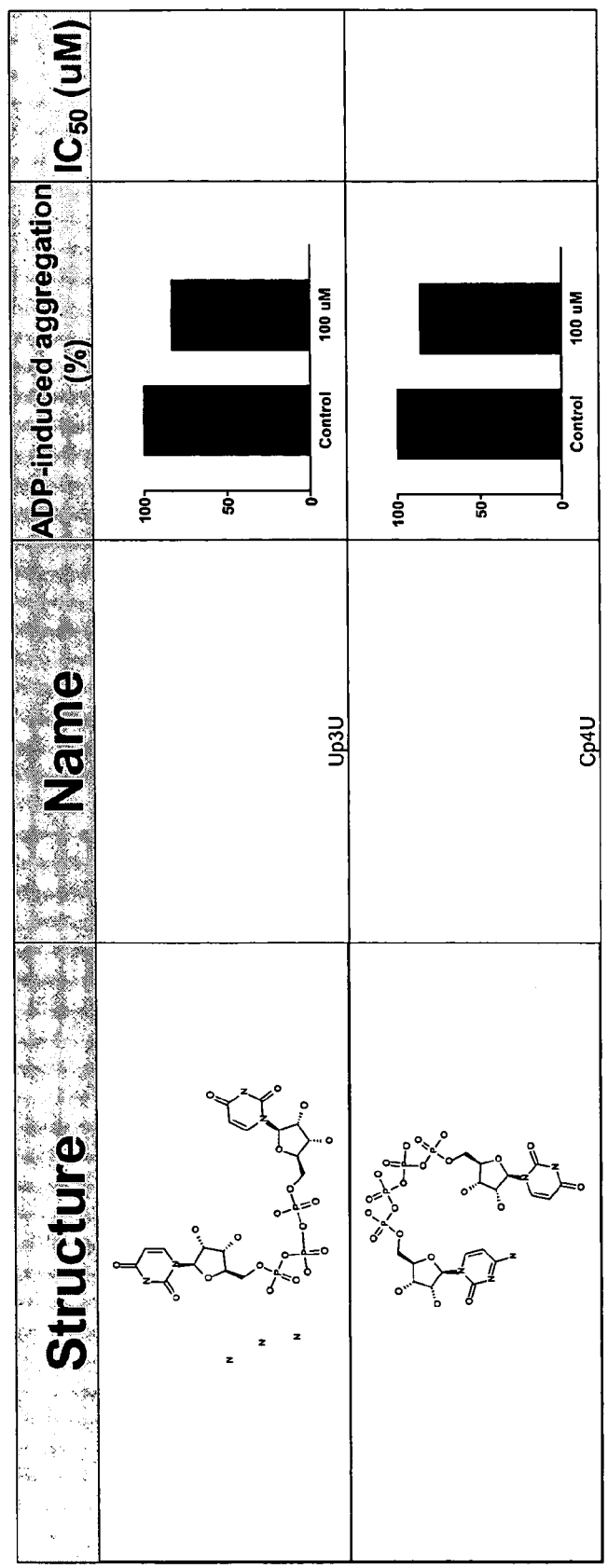

This invention is provides a method of preventing or treating diseases or conditions associated with platelet aggregation. The method also provides a method of treating thrombosis. The method comprises administering to a subject a pharmaceutical composition comprising a therapeutic effective amount of P2Y$_{12}$ receptor antagonist compound, wherein said amount is effective to bind the P2Y$_{12}$ receptors on platelets and inhibit ADP-induced platelet aggregation. The P2Y$_{12}$ receptor antagonist compounds useful for this invention include compound of general Formula I and salts thereof:

Formula I

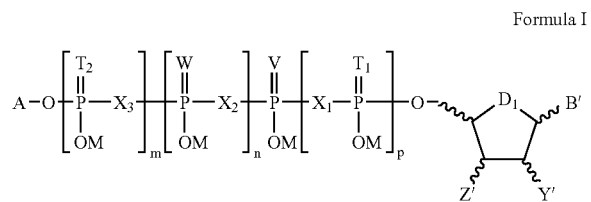

wherein:

$X_1$, $X_2$, and $X_3$ are independently oxygen, methylene, monochloromethylene, dichloromethylene, monofluoromethylene, difluoromethylene, or imido;

$T_1$, $T_2$, W, and V are independently oxygen or sulfur;

m=0, 1 or 2;

n=0 or 1;

p=0, 1, or 2;

where the sum of m+n+p is from 0 to 5; (from monophosphate to hexaphosphate) M=H, or a pharmaceutically-acceptable inorganic or organic counterion;

D=O or $CH_2$

B' is a purine or a pyrimidine residue according to general Formulae IV and V which is linked to the 1'-position of the furanose or carbocycle via the 9- or 1-position of the base, respectively;

Y'=H, OH, or $OR_1$;

Z'=H, OH, or $OR_2$; with the proviso that when A=M, at least one of Y' and Z' is $OR_1$ or $OR_2$;

A=M, or

A is a nucleoside residue which is defined as:

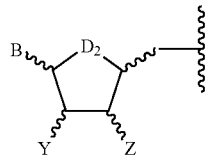

and which is linked to the phosphate chain via the 5'-position of the furanose or carbocycle;

wherein:

$D_2$=O or $CH_2$;

Z=H, OH, or $OR_3$;

Y=H, OH, or $OR_4$;

with the proviso that at least one of Y', Z', Y and Z is equal to $OR_1$, $OR_2$, $OR_4$ or $OR_3$ respectively.

B is a purine or a pyrimidine residue according to general Formulae IV and V which is linked to the 1' position of the furanose or carbocycle via the 9- or 1-position of the base, respectively;

$R_1$, $R_2$, $R_3$, and/or $R_4$ are residues which are linked directly to the 2'- and/or 3'-hydroxyls of the respective furanose or carbocycle via a carbon atom according to Formula II, or linked directly to two (2'- and 3'-)hydroxyls of the respective furanose or carbocycle via a common carbon atom according to Formula II, such that from one to four independent residues of $R_1$, $R_2$, $R_3$ and $R_4$ falling within the definition of Formula II are present or from one to two independent residues made up of $R_1$+$R_2$ and/or $R_3$+$R_4$ are present;

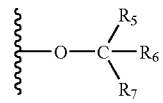

Formula II wherein:

O is the corresponding 2'- and/or 3'-oxygen of the respective furanose or carbocycle;

C is a carbon atom;

$R_5$, $R_6$, and $R_7$ are H, alkyl, cycloalkyl, aralkyl, aryl, substituted aralkyl, or substituted aryl, such that the moiety defined according to Formula II is an ether; or $R_5$ and $R_6$ are H, an alkyl, cycloalkyl, aralkyl, aryl, substituted aralkyl, or substituted aryl, and $R_7$ is alkoxy, cycloalkoxy, aralkyloxy, aryloxy, substituted aralkyloxy, or substituted aryloxy such that the moiety defined according to Formula II is an acyclic acetal or ketal; or $R_5$ and $R_6$ are taken together as oxygen or sulfur doubly bonded to C, and $R_7$ is alkyl, cycloalkyl, aralkyl, aryl, substituted aralkyl, or substituted aryl, such that the moiety defined according to Formula II is an ester or thioester; or $R_5$ and $R_6$ are taken together as oxygen or sulfur doubly bonded to C, and $R_7$ is amino or mono- or disubstituted amino, where the substituents are alkyl, cycloalkyl, aralkyl, aryl, substituted aralkyl, or substituted aryl, such that the moiety according to Formula II is a carbamate or thiocarbamate; or $R_5$ and $R_6$ are taken together as oxygen or sulfur doubly bonded to C, and $R_7$ is alkoxy, cycloalkoxy, aralkyloxy, aryloxy, substituted aralkyloxy, or substituted aryloxy, such that the moiety according to Formula II is a carbonate or thiocarbonate; or $R_7$ is not present and $R_5$ and $R_6$ are taken together as oxygen or sulfur doubly bonded to C and both the 2'- and 3'-oxygens of the respective furanose or carbocycle are directly bound to C to form a cyclical carbonate or thiocarbonate;

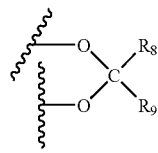

Formula III wherein:

the O atoms are the 2'- and 3'-oxygens of a furanose or carbocycle; and the 2'- and 3'-oxygens of the furanose or carbocycle are linked by a common carbon atom (C) to form a cyclical acetal, cyclical ketal, or cyclical orthoester;

for cyclical acetals and ketals, $R_8$ and $R_9$ are independently hydrogen, alkyl, cycloalkyl, aralkyl, aryl, substituted aralkyl, substituted aryl, or can be joined together to form a homocyclic or heterocyclic ring composed of 3 to 8 atoms, preferably 3 to 6 atoms;

for cyclical orthoesters, $R_8$ is hydrogen, alkyl, cycloalkyl, aralkyl, aryl, substituted aralkyl, or substituted aryl, $R_9$ is alkyloxy, cycloalkyloxy, aralkyloxy, aryloxy, substituted aralkyloxy, or substituted aryloxy.

when present, the alkyl, cycloalkyl, aralkyl, aryl, substituted aralkyl and substituted aryl components of $R_5$ to $R_9$ can be generally defined as, but are not limited to, the following:

alkyl groups are from 1 to 12 carbons inclusively, either straight chained or branched, with or without unsaturation and with or without heteroatoms, are more preferably from 2 to 8 carbons inclusively, and most preferably 2 to 6 carbons inclusively;

cycloalkyl groups from 3 to 12 carbons inclusively, more preferably from 3 to 10 carbons inclusively, and most preferably 3 to 6 carbons inclusively, with or without unsaturation, and with or without heteroatoms;

aralkyl groups are from 1 to 8 carbons inclusively in the alkyl portion, are more preferably from 1 to 6 carbons inclusively in the alkyl portion, and most preferably are 1 to 4 carbons inclusively in the alkyl portion; as included in the alkyl definition above, the alkyl portion of an aralkyl group can include one or more positions of unsaturation such as a double bonds or a triple bond in the chain when the chain includes two or more carbon atoms; the alkyl portion of an aralkyl group can also include one or more heteroatoms and/or substituents; the aryl portion of an aralkyl group can be a monocyclic or polycyclic moiety from 3 to 8 carbons inclusively per ring in the aryl portion, more preferably from 4 to 6 carbons inclusively per ring, and most preferably 5 to 6 carbons inclusively per ring; the aryl portion of an aralkyl group can also bear one or more substituents and/or heteroatoms;

aryl groups are either monocyclic or polycyclic, are from 3 to 8 carbons inclusively per ring, are more preferably from 4 to 6 carbons inclusively per ring, and are most preferably 5 to 6 carbons inclusively per ring; aryl groups can also bear substituents and/or heteroatoms.

Preferred substituents on the foregoing groups can be, but are not limited to, hydroxy, nitro, methoxy, fluoro, chloro, bromo, iodo, methyl, ethyl, propyl, butyl, thioalkyl, alkoxy, carboxyl, cyano, amino, substituted amino, trifluoromethyl, phenyl, cyclopropyl, cyclopentyl, and cyclohexyl; and preferred heteroatoms are oxygen, nitrogen, and sulfur.

When $R_5$, $R_6$ and $R_7$ are not the same, or when $R_8$ and $R_9$ are not the same, a compound according to Formula I can exist in several diastereomeric forms. The general structure of Formula I includes all diastereomeric forms of such materials, when not specified otherwise. Formula I also includes mixtures of compounds of Formula I, including mixtures of enantiomers, diastereomers and/or other isomers in any proportion.

One embodiment of the invention is that A═M, wherein M═H or a pharmaceutically-acceptable inorganic or organic counterion. In such an embodiment, the compound can be a nucleoside monophosphate, nucleoside diphosphate, nucleoside triphosphate, nucleoside tetraphosphate, nucleoside pentaphosphate, or nucleoside hexaphosphate with one or both of the 2'- and/or 3'-positions of the furanose or carbocycle modified. Most preferred are nucleotide monophosphates, nucleotide diphosphates, nucleotide triphosphates, and nucleotide tetraphosphates. When $T_2$, W, V, or $T_1$ are sulfur, the preferred position for this atom is on the terminal phosphorous of the polyphosphate chain (i.e. the phosphorous furthest removed from the nucleoside residue).

For monophosphates, where m, n, and p are all equal to zero, preferably $R_8$ is hydrogen and $R_9$ is aryl or aralkyl, with 1, 2, 3, or 4 carbons inclusively in the alkyl portion of an aralkyl group, and 6 carbons inclusively in the aryl portion of an aralkyl or aryl group; when the number of carbons in the alkyl portion of an aralkyl group is 2, the carbon atoms are most preferably connected by either a double or triple bond.

Another embodiment of the invention is that A is a nucleoside residue defined as:

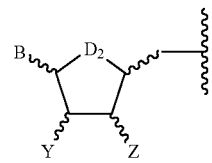

and linked to the phosphate chain via the 5'-position of the furanose or carbocycle (to give a dinucleoside polyphosphate with at least one of the 2'-, 3'-, 2"- and 3"-positions of the furanose or carbocycle moieties modified to be $OR_1$, $OR_2$, $OR_4$ or $OR_3$ respectively).

When $T_2$, W, V, and/or $T_1$ are sulfur, the preferred positions (for sulfur) are $T_1$ and $T_2$.

Further provisions are that when either $D_1$ or $D_2$ are oxygen, the corresponding furanose is preferably in the β-configuration; and that the corresponding furanose is most preferably in the β-D-configuration.

Preferred compounds of general Formula I are molecules whose structures fall within the definitions of Formula Ia and Formula Ib:

Formula Ia

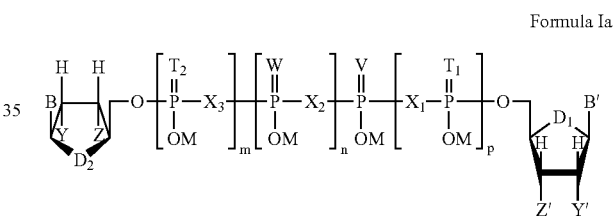

wherein:
$D_1$═O or $CH_2$;
$D_2$═O or $CH_2$;
B and B' are independently purine or pyrimidine residues according to general Formula IV or V;
m and p═0, 1 or 2; n═0 or 1; such that the sum of m+n+p is from 0 to 5, preferably 0 to 4, and most preferably 0 to 3;
$X_1$, $X_2$, and $X_3$═are independently O, NH, $CH_2$, CHF, CHCl, $CF_2$, $CCl_2$;
$T_1$, $T_2$, V, and W are independently O or S;
M═$H^+$, $NH_4^+$, $Na^+$ or other pharmaceutically-acceptable inorganic or organic counter ion;
Y'═H, OH, or $OR_1$;
Z'═OH or $OR_2$;
Z═OH or $OR_3$;
Y═H, OH, or $OR_4$, where $R_1$, $R_2$, $R_3$ and $R_4$ fall under the definition of general Formulae II or III, provided that at least one of Y', Z', Z and Y is $OR_1$, $OR_2$, $OR_3$, or $OR_4$.

Preferred compounds of Formula Ia include:
$D_1$═O or $CH_2$;
$D_2$═O or $CH_2$;
$X_1$, $X_2$, and $X_3$═O;
$T_1$, $T_2$, V, and W═O; or
$D_1$═O or $CH_2$;
$D_2$═O or $CH_2$;
$X_1$ and $X_3$═O;

$X_2$=methylene, monochloromethylene, dichloromethylene, monofluoromethylene, difluoromethylene, or imido;
$T$, $T_1$, $T_2$, $V$, and $W$=O; or
$D_1$=O or $CH_2$;
$D_2$=O or $CH_2$;
m, n, and p=1; or
$X_1$ and $X_3$=O;
$X_2$=methylene, monochloromethylene, dichloromethylene, monofluoromethylene, difluoromethylene, or imido;
$T_1$ and $T_2$=S;
$V$ and $W$=O.

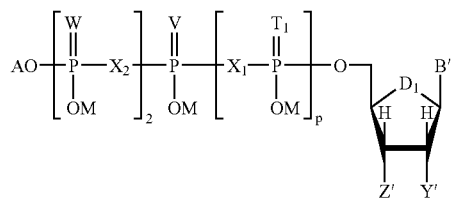

Formula Ib

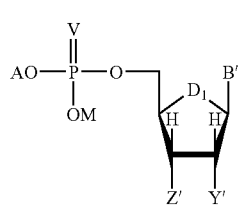

Formula Ib'

For compounds of Formula I, B and B' can independently be a purine residue, as in Formula IV, linked through the 9-position, or a pyrimidine residue, as in Formula V, linked through the 1-position. The ribosyl moieties in Formulae Ia, Ib, and Ib' are in the D-configuration as shown, but can also be L-, or D- and L-. The D-configuration is preferred for ribosyl moieties.

$D_1$=O or $CH_2$;
n and p=0, 1, or 2 such that the sum of n+p is from 0 to 3;
A=M; wherein M=$H^+$, $NH_4^+$, $Na^+$ or other pharmaceutically-acceptable inorganic or organic counterion;
B' is a purine or pyrimidine residue according to general Formulae IV and V;
$X_1$ and $X_2$ are independently O, NH, $CH_2$, CHF, CHCl, $CF_2$, $CCl_2$;
$T_1$, $V$, and $W$ are independently O or S;
Y'=H, OH, or $OR_1$
Z'=H, OH or $OR_2$, where $R_1$ and $R_2$ fall under the definitions of general Formulae II or III; with the proviso that at least one of Y' and Z' is OR$_1$ or OR$_2$, respectively.

Preferred compounds of Formula Ib include:
$D_1$=O or $CH_2$;
n and p=0, 1, or 2 such that the sum of n+p is from 0 to 3, preferably 1 to 2;
$X_1$ and $X_2$=O;
$T_1$, $V$, and $W$=O; or
$D_1$=O or $CH_2$;
$X_1$ and $X_2$=O;
$T_1$ and $V$=O;
$W$=S; or
$D_1$=O;
n and p=0 such that the sum of n+p is 0;
$V$=O;
B' is a purine residue of general Formula IV;
Y' and Z' fall under the definition of general Formula III;
or
$D_1$=O or $CH_2$;
p=0, 1, or 2, n=1, such that the sum of n+p is from 1 to 3;
$X_1$=O;
$X_2$=methylene, monochloromethylene, dichloromethylene, monofluoromethylene, difluoromethylene, or imido;
$T_1$, $V$, and $W$=O;
Y'=H, OH, or $OR_1$;
Z'=H, OH or $OR_2$, where $R_1$ and $R_2$ fall under the definition of general Formulae II or III; with the proviso that at least one of Y' and Z' is OR$_1$ or OR$_2$, respectively.

Several preferred compounds also are described by Formula Ib':

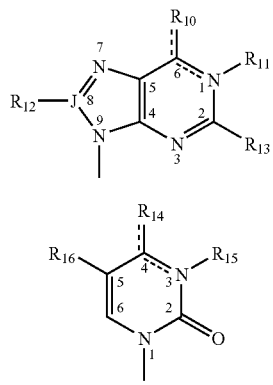

Formula IV

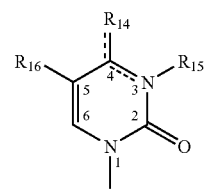

Formula V wherein:
$R_{10}$ and $R_{14}$ independently are hydroxy, oxo, amino, mercapto, alkylthio, alkyloxy, aryloxy, alkylamino, cycloalkylamino, aralkylamino, arylamino, diaralkylamino, diarylamino, or dialkylamino, where the alkyl groups are optionally linked to form a heterocycle; or $R_{10}$ and $R_{14}$ independently are acylamino, provided that they incorporate an amino residue from the C-6 position of the purine or the C-4 position of the pyrimidine; or when $R_{10}$ in a purine or $R_{14}$ in a pyrimidine has as its first atom nitrogen, $R_{10}$ and $R_{11}$ or $R_{14}$ and $R_{15}$ can be taken together to form a 5-membered fused imidazole ring (to give an etheno compound), optionally substituted on the etheno ring with one or more alkyl, cycloalkyl, aralkyl, or aryl moieties, as described for $R_5$–$R_9$ above;

J is carbon or nitrogen, with the provision that when J=nitrogen, $R_{12}$ is not present;

$R_{11}$ is hydrogen, 0 (adenine 1-oxide derivatives) or is absent (adenine derivatives);

$R_{15}$ is hydrogen, or acyl (e.g. acetyl, benzoyl, phenylacyl, with or without substituents);

$R_{12}$ is hydrogen, alkyl, bromo, azido, alkylamino, arylamino or aralkylamino, alkoxy, aryloxy or aralkyloxy, alkylthio, arythio or aralkylthio, or ω-A($C_{1-6}$alkyl)B-, wherein A and B are independently amino, mercapto, hydroxy or carboxyl;

$R_{13}$ is hydrogen, chlorine, amino, monosubstituted amino, disubstituted amino, alkylthio, arylthio, or aralkylthio, where the substituent on sulfur contains up to a maximum of 20 carbon atoms, with or without unsaturation, and with or without substituents on the chain;

$R_{16}$ is hydrogen, methyl, alkyl, halogen, alkyl, alkenyl, substituted alkenyl, alkynyl, or substituted alkynyl.

Compounds according to Formulae IV and V where $R_{10}$ or $R_{14}$ is acylamino fall within the scope of Formula VI:

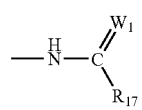

Formula VI wherein:

NH is the amino residue at the C-6 position in a purine or the amino residue at the C-4 position in a pyrimidine;

C is a carbon atom;

$W_1$ is oxygen or sulfur;

$R_{17}$ is amino or mono- or disubstituted amino, with the amino substituent(s) being alkyl, cycloalkyl, aralkyl, or aryl, with or without further substituents, unsaturation, or heteroatoms, such that the moiety according to Formula VI is a urea or thiourea; or $R_{17}$ is alkoxy, aralkyloxy, aryloxy, substituted aralkyloxy, or substituted aryloxy, such that the moiety according to Formula VI is a carbamate or thiocarbamate; or $R_{17}$ is alkyl, cycloalkyl, aralkyl, or aryl, with or without substituents or heteroatoms, such that the moiety according to Formula VI is an amide; with definitions of alkyl, cycloalkyl, aralkyl, or aryl groups as previously defined for comparable groups in $R_5$ to $R_9$ The compounds of the present invention can be conveniently synthesized by those skilled in the art using well-known chemical procedures. Mononucloside mono-, di- and triphosphates can be obtained from commercial sources or can be synthesized from the nucleoside using a variety of phosphorylation reactions which can be found in the chemical literature. Symmetrical and unsymmetrical dinucleotide polyphosphates can be prepared by activation of a nucleoside mono-, di- or triphosphate with a coupling agent such as, but not limited to, dicyclohexylcarbodiimide or 1,1'-carbonyldiimidazole, followed by condensation with another nucleoside mono-, di-, or triphosphate, which can be the same or different as the activated moiety. Activation of nucleoside triphosphates with dicyclohexylcarbodiimide gives a cyclical trimetaphosphate as the activated species, which can be advantageously reacted with a variety of nucleophiles to install unique substituents on the terminal phosphate of a triphosphate.

The compounds of the present invention can be prepared by derivatization or substitution at the level of the nucleoside, followed by phosphorylation and condensation as previously described, or the reactions can be carried out directly on the preformed mono- or dinucleotides. In the general Formulae Ia and Ib, the substituents at Y', Z', Y, and Z can be esters, carbamates, or carbonates, which are generally described by Formula II. Esters can be readily prepared by reacting a hydroxyl group of the furanose in a nucleoside or nucleotide with an activated form of an appropriate organic acid, such as an acid halide or acid anhydride in the presence of an organic or inorganic base. Alternately, use of a suitable coupling reagent such as dicyclohexylcarbodiimide, 1,1'-carbonyldiimidazole and the like to activate the organic acid can be used to achieve the same result.

Carbamates or thiocarbamates can be most conveniently prepared by reaction of a hydroxyl group of the furanose in a nucleoside or nucleotide with any of a number of commercially available isocyanates or isothiocyanates, respectively, in an inert solvent. Alternately, when a desired isocyanate or isothiocyanate cannot be obtained from commercial sources, it can be prepared from the corresponding amine by the use of phosgene or thiophosgene, respectively, or their chemical equivalents. Carbonates or thiocarbonates can be synthesized by reacting the hydroxyl groups of a furanose in a nucleoside or nucleotide with an appropriate haloformate in the presence of an organic or inorganic base.

In the general Formulae Ia, Ib and Ib', the substituents at Y'and Z', and Y and Z, when taken together, can be taken to mean acetals, ketals or orthoesters, as described in Formula III. Acetals and ketals can be readily prepared by reaction of the neighboring 2'- and 3'-hydroxyl groups of the furanose in an appropriate nucleoside or nucleotide with an aldehyde or ketone, respectively, or their chemical equivalents, in the presence of an acid catalyst. Particularly advantageous is the use of an organic acid, which can effect the transformation without affecting the integrity of the rest of the molecule. Alternately, strong acids such as trichloroacetic, p-toluenesulfonic, methanesulfonic and the like can be employed in catalytic amounts, in conjunction with inert solvents. Most preferred is formic acid, which can be removed by evaporation under reduced pressure, and is ideally suited to serve as both solvent and catalyst for these reactions. Alternately, trifluoroacetic acid can be substituted for formic acid in the reaction, provided that the reaction is carried out at low temperatures and the aldehyde or aldehyde equivalent used to prepare the acetal is stable to strong acid conditions. The discovery of the utility of formic acid and trifluoroacetic acid for this purpose is one particular aspect of this invention.

Cyclical orthoesters can be prepared by reaction of the neighboring 2'- and 3'-hydroxyl groups of a furanose with an acylic orthoester, in the presence of an acid. When the nucleoside or nucleotide to be derivatized is a purine that contains a 6-amino functionality or is a pyrimidine that contains a 4-amino functionality, it can be converted to the respective urea or thiourea by treatment with an isocyanate or isothiocyanate, respectively, as was previously described for carbamates or thiocarbamates of the 2'- or 3'-hydroxyls of a furanose. It was found that reactions of such an amino group with isocyanates or isothiocyanates can be carried out in the presence of one or more hydroxyl groups on a furanose, by appropriate manipulation of the stoichiometry of the reaction.

All of the derivitization reactions described herein can be carried out on preformed dinucleotide polyphosphates, which results in multiple products dependent on reaction stoichiometry and on whether multiple reactive groups are present. When multiple products are obtained, these can be conveniently separated by the use of preparative reverse phase high performance liquid chromatography (HPLC). Particularly advantageous is the use of C 18 or phenyl reverse phase columns, in conjunction with gradients that start with ammonium acetate buffer and end with methanol. The use of a buffer provides for nucleotide stability and improved peak shape of the eluting products and the use of methanol allows for effective desorption of these lipophilic compounds from the column. Particularly advantageous is the use of ammonium acetate buffer solutions in conjunction with methanol, as these solvents are miscible in all proportions and can be readily removed from the chromatographed products by evaporation, followed by lyophilization.

While separation of multiple products can be done by HPLC, another strategy is to use nucleosides or nucleotides which contain only a single reactive functionality, whether because only one is present, or by the use of protecting groups to block side reactions at other positions in the molecule. This can be done at the level of preformed dinucleotide polyphosphates, or alternately, can be carried out on nucleoside mono-, di-, or triphosphates, leading to novel products in their own right, or can be coupled to other nucleoside mono-, di, or triphosphates by the methods which have already been described.

It will be recognized by those skilled in the art that the above reactions and purification techniques can also be applied to carba-ribose analogues (e.g., $D_1=CH_2$) of nucleosides, nucleotides and their derivatives, and that the terms such as "mononucleotide" and "dinucleotide" also apply to the carba-ribose analogues and other derivatives defined by Formulae I–IV.

The inventors of the present invention have discovered compounds that are antagonists of the effect of ADP on its platelet membrane receptor, the $P2Y_{12}$ receptor. The compounds provide efficacy as antithrombotic agents by their ability to block ADP from acting at its platelet receptor site and thus prevent platelet aggregation. Thus, these compounds can provide a more efficacious antithrombotic effect than aspirin, but with less profound effects on bleeding than antagonists of the fibrinogen receptor. Since ADP-induced platelet aggregation is mediated by the simultaneous activation of both $P2Y_{12}$ and $P2Y_1$ receptors, the combined administration of the compounds described here with antagonists of platelet $P2Y_1$ receptors could potentially provide a more efficacious antithrombotic effect at concentrations of each antagonist that are below the effective concentrations to block each receptor subtype in other systems, resulting in a decrease of the potential manifestation of adverse effects. In addition, these compounds can be used in conjunction with lower doses of other platelet aggregation inhibitors which work by different mechanisms, to reduce the possible side effects of said agents. Finally, if the compounds of the present invention have sufficient binding affinity and bear a fluorescent moiety, they can find uses as biochemical probes for the $P2Y_{12}$ receptor.

The compounds of the present invention fall under the definition of general Formula I which is further divided into general Formulae Ia (dinucleotides), Ib (mononucleotides) and Ib' (mononucleotide monophosphates). While potent and selective $P2Y_{12}$ antagonists can be found within either of these subdivisions, mononucleotides have an advantage over dinucleotides in terms of ease of synthesis and cost. In general, diphosphates and triphosphates falling under general Formula Ib are more potent antagonists at $P2Y_{12}$ than the corresponding monophosphates of Formula Ib'. However, nucleoside 5'-monophosphates and their analogues are easier to prepare and have greater chemical and biological stability. Thus, for synthetic reasons, a nucleoside 5'-monophosphate with appropriate druglike properties is sometimes more advantageous than other mononucleotides bearing more than one phosphate, or related dinucleotides.

Two preferred modifications falling under the definition of general Formula Ib' can be made to nucleoside 5'-monophosphates to render them antagonists of the platelet $P2Y_{12}$ receptor. In general, the preferred nucleoside 5'-monophosphate starting material chosen for this purpose is AMP, or an adenosine 5'-monophosphate derivative, as it contains the appropriate functional groups for the desired modifications and gives rise to more potent and selective antagonists compared to similar modifications of other commonly available nucleotide monophosphates. The first preferred modification is to install an aryl or aralkyl acetal bridging the 2'- and 3'-hydroxyls of the ribose, with the nature of the aryl or aralkyl group as previously described. The second modification is to add an aminocarbonyl or substituted aminocarbonyl group to the 6-amino position of the adenine base, resulting in a urea moiety at that position. Substituents on the urea moiety fall under the definition of $R_{17}$, as previously described. These urea substituents can be broadly categorized as either aromatic or aliphatic in nature. Generally, the most preferred substituent chosen from aryl groups is phenyl. When the urea group is an aliphatic urea, the preferred substituents on nitrogen are linear, branched, or cyclic, having from 1 to 6 carbons on the alkyl substituent, and with or without unsaturation. More preferred are linear alkyl ureas from 2 to 6 carbons inclusively, or cyclic alkyl ureas having 3 to 6 carbons in the ring; most preferred are linear alkyl ureas containing from 2 to 4 carbons inclusively in the chain or cycloalkyl ureas having from 3 to 5 carbons inclusively in the ring.

An important aspect of the present invention is that, while any of the described modifications alone can result in a compound capable of antagonism of ADP-induced platelet aggregation, it is the combination of both 2'/3' and 6-N modifications in the same molecule that renders the nucleotide a highly potent and selective $P2Y_{12}$ antagonist.

Another important aspect of the present invention is the effect of compound structure on the resultant potency in washed platelets versus potency in whole blood. In general, the potency of a given compound is lower in whole blood versus washed platelets, ostensibly the result of increased binding of the compound to the higher levels of blood proteins in the former. This property is particularly acute for nucleoside 5'-monophosphates versus the corresponding di- and triphosphates, since there are fewer ionizable groups available in the former to offset the lipophilic acetal and urea groups which, presumably, increase protein binding in whole blood. Unexpectedly, we found that compounds containing phenyl ureas exhibited a greater loss of potency in whole blood compared to their activity in washed platelets, while those derivatives having aliphatic ureas gave more comparable results when tested in whole blood and washed platelet assays. Furthermore, compounds with aliphatic ureas were significantly more potent than their aromatic counterparts in washed platelets. Taken together, these findings enabled the discovery of the most potent and selective compounds of the present invention.

The compounds of general Formula I are useful in therapy, in particular in the prevention of platelet aggregation. The compounds of the present invention are thus useful as anti-thrombotic agents, and are thus useful in the treatment or prevention of unstable angina, coronary angioplasty (PTCA) and myocardial infarction.

The compounds of the present invention are also useful in the treatment or prevention of primary arterial thrombotic complications of atherosclerosis such as thrombotic stroke, peripheral vascular disease, myocardial infarction without thrombolysis.

Still further indications where the compounds of the invention are useful are for the treatment or prevention of arterial thrombotic complications due to interventions in atherosclerotic disease such as angioplasty, endarterectomy, stent placement, coronary and other vascular graft surgery.

Still further indications where the compounds of the invention are useful are for the treatment or prevention of thrombotic complications of surgical or mechanical damage such as tissue salvage following surgical or accidental trauma, reconstructive surgery including skin flaps, and "reductive" surgery such as breast reduction.

The compounds of the present invention are also useful for the prevention of mechanically-induced platelet activation in vivo such as cardiopulmonary bypass (prevention of microthromboembolism), prevention of mechanically-induced platelet activation in vitro such as the use of the compounds in the preservation of blood products, e.g. platelet concentrates, prevention of shunt occlusion such as renal dialysis and plasmapheresis, thrombosis secondary to vascular damage/inflammation such as vasculitis, arteritis, glomerulonephritis and organ graft rejection.

Still further indications where the compounds of the present invention are useful are indications with a diffuse thrombotic/platelet consumption component such as disseminated intravascular coagulation, thrombotic thrombocytopenic purpura, hemolytic uremic syndrome, heparin-induced thrombocytopenia and pre-eclampsia/eclampsia.

Still further indications where the compounds of the invention are useful are for the treatment or prevention of venous thrombosis such as deep vein thrombosis, veno-occlusive disease, hematological conditions such as thrombocythemia and polycythemia, and migraine.

In a particularly preferred embodiment of the present invention, the compounds are used in the treatment of unstable angina, coronary angioplasty and myocardial infarction.

In another particularly preferred embodiment of the present invention, the compounds are useful as adjunctive therapy in the prevention of coronary arterial thrombosis during the management of unstable angina, coronary angioplasty and acute myocardial infarction, i.e. perithrombolysis. Agents commonly used for adjunctive therapy in the treatment of thrombotic disorders can be used, for example heparin and/or aspirin, just to mention a few.

A method of treating a mammal to alleviate the pathological effects of atherosclerosis and arteriosclerosis, acute MI, chronic stable angina, unstable angina, transient ischemic attacks and strokes, peripheral vascular disease, arterial thrombosis, preeclampsia, embolism, restenosis or abrupt closure following angioplasty, carotid endarterectomy, and anastomosis of vascular grafts.

The compounds of this invention can be used in vitro to inhibit the aggregation of platelets in blood and blood products, e.g. for storage, or for ex vivo manipulations such as in diagnostic or research use. This invention also provides a method of inhibiting platelet aggregation and clot formation in a mammal, especially a human, which comprises the internal administration of a compound of Formula (I) and a pharmaceutically acceptable carrier.

Chronic or acute states of hyper-aggregability, such as disseminated intravascular coagulation (DIC), septicemia, surgical or infectious shock, post-operative and post-partum trauma, cardiopulmonary bypass surgery, incompatible blood transfusion, abruptio placenta, thrombotic thrombocytopenic purpura (TTP), snake venom and immune diseases, are likely to be responsive to such treatment.

This invention further provides a method for inhibiting the reocclusion of an artery or vein following fibrinolytic therapy, which comprises internal administration of a compound of Formula (I) and a fibrinolytic agent. When used in the context of this invention, the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and mutants, or variants thereof, which retain plasminogen activator activity, such as variants which have been chemically modified or in which one or more amino acids have been added, deleted or substituted or in which one or more functional domains have been added, deleted or altered such as by combining the active site of one plasminogen activator or fibrin binding domain of another plasminogen activator or fibrin binding molecule.

Extracorporeal circulation is routinely used for cardiovascular surgery in order to oxygenate blood. Platelets adhere to surfaces of the extracorporeal circuit. Platelets released from artificial surfaces show impaired hemostatic function. Compounds of the invention can be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty of coronary and other arteries and after coronary artery bypass procedures.

The compounds of the present invention also encompass their non-toxic pharmaceutically acceptable salts, such as, but not limited to, an alkali metal salt such as sodium or potassium; an alkaline earth metal salt such as manganese, magnesium or calcium; or an ammonium or tetraalkyl ammonium salt, i.e., $NX_4^+$ (wherein X is $C_{1-4}$). Pharmaceutically acceptable salts are salts that retain the desired biological activity of the parent compound and do not impart undesired toxicological effects.

Those skilled in the art will recognize various synthetic methodologies which can be employed to prepare non-toxic pharmaceutically acceptable salts and acylated prodrugs of the compounds.

The active compounds can be administered systemically to target sites in a subject in need such that the extracellular concentration of a $P2Y_{12}$ agonist is elevated to block the binding of ADP to $P2Y_{12}$ receptor, thus inhibit the platelet aggregation. The term systemic as used herein includes subcutaneous injection, intravenous, intramuscular, intrastemal injection, intravitreal injection, infusion, inhalation, transdermal administration, oral administration, rectal administration and intra-operative instillation.

For systemic administration such as injection and infusion, the pharmaceutical formulation is prepared in a sterile medium. The active ingredient, depending on the vehicle and concentration used, can either be suspended or dissolved in the vehicle. Adjuvants such as local anesthetics, preservatives and buffering agents can also be dissolved in the vehicle. The sterile indictable preparation can be a sterile indictable solution or suspension in a non-toxic acceptable diligent or solvent. Among the acceptable vehicles and solvents that can be employed are sterile water, saline solution, or Ringer's solution.

Another method of systemic administration of the active compound involves oral administration, in which pharmaceutical compositions containing active compounds are in the form of tablets, lozenges, aqueous or oily suspensions, viscous gels, chewable gums, dispersible powders or granules, emulsion, hard or soft capsules, or syrups or elixirs.

For oral use, an aqueous suspension is prepared by addition of water to dispersible powders and granules with a dispersing or wetting agent, suspending agent one or more preservatives, and other excipients. Suspending agents include, for example, sodium carboxymethylcellulose, methylcellulose and sodium alginate. Dispersing or wetting agents include naturally-occurring phosphatides, condensation products of an allylene oxide with fatty acids, condensation products of ethylene oxide with long chain aliphatic alcohols, condensation products of ethylene oxide with partial esters from fatty acids and a hexitol, and condensation products of ethylene oxide with partial esters derived from fatty acids and hexitol anydrides. Preservatives include, for example, ethyl, and n-propyl p-hydroxybenzoate. Other excipients include sweetening agents (e.g., sucrose, saccharin), flavoring agents and coloring agents. Those skilled in the art will recognize the many specific excipients and wetting agents encompassed by the general description above.

For oral application, tablets are prepared by mixing the active compound with nontoxic pharmaceutically acceptable excipients suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets can be uncoated or they can be coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Formulation for oral use can also be presented as chewable gums by embedding the active ingredient in gums so that the active ingredient is slowly released upon chewing.

Additional means of systemic administration of the active compound to the target platelets of the subject would involve a suppository form of the active compound, such that a therapeutically effective amount of the compound reaches the target sites via systemic absorption and circulation.

For rectal administration, the compositions in the form of suppositories can be prepared by mixing the active ingredient with a suitable non-irritating excipient which is solid at ordinary temperatures but liquid at the rectal temperature and will therefore melt in the rectum to release the compound. Such excipients include cocoa butter and polyethylene glycols.

The active compounds can also be systemically administered to the platelet aggregation sites through absorption by the skin using transdermal patches or pads. The active compounds are absorbed into the bloodstream through the skin. Plasma concentration of the active compounds can be controlled by using patches containing different concentrations of active compounds.

One systemic method involves an aerosol suspension of respirable particles comprising the active compound, which the subject inhales. The active compound would be absorbed into the bloodstream via the lungs, and subsequently contact the target platelets in a pharmaceutically effective amount. The respirable particles can be liquid or solid, with a particle size sufficiently small to pass through the mouth and larynx upon inhalation; in general, particles ranging from about 1 to 10 microns, but more preferably 1–5 microns, in size are considered respirable.

Another method of systemically administering the active compounds to the platelet aggregation sites of the subject involves administering a liquid/liquid suspension in the form of eye drops or eye wash or nasal drops of a liquid formulation, or a nasal spray of respirable particles that the subject inhales. Liquid pharmaceutical compositions of the active compound for producing a nasal spray or nasal or eye drops can be prepared by combining the active compound with a suitable vehicle, such as sterile pyrogen free water or sterile saline by techniques known to those skilled in the art.

Intravitreal delivery can include single or multiple intravitreal injections, or via an implantable intravitreal device that releases $P2Y_{12}$ antagonists in a sustained capacity. Intravitreal delivery can also include delivery during surgical manipulations as either an adjunct to the intraocular irrigation solution or applied directly to the vitreous during the surgical procedure.

For systemic administration, plasma concentrations of active compounds delivered can vary according to compounds; but are generally $1 \times 10^{-10} - 1 \times 10^{-5}$ moles/liter, and preferably $1 \times 10^{-8} - 1 \times 10^{-6}$ moles/liter.

The pharmaceutical utility of $P2Y_{12}$ antagonist compounds of this invention is indicated by their inhibition of ADP-induced platelet aggregation. This widely used assay, as described in S. M. O. Hourani et al. *Br. J. Pharmacol.* 105, 453–457 (1992) relies on the measurement of the aggregation of a platelet suspension upon the addition of an aggregating agent such as ADP.

The present invention also provides novel compounds. The present invention additionally provides novel pharamaceutical formulations comprising compounds of Formula I of high purity, and/or in a pharmaceutically acceptable carrier. The pharmaceutically acceptable carrier can be selected by those skilled in the art using conventional criteria. The pharmaceutically acceptable carrier include, but are not limited to, saline and aqueous electrolyte solutions, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

Novel compounds of the present invention include compounds of Formula Ib (mononucleotide), provided that when n=1, both $X_1$ and $X_2$ are not 0; and when n=0, $X_1$ is not 0; and provided when Y'=H, that $X_2$ is independently O, $CH_2$, CHF, CHCl, $CF_2$, $CCl_2$; also provided that when $R_{10}$=$NH_2$ or 0, and when $R_5$ and $R_6$ are taken together as oxygen doubly bonded to C, then $R_7$ is not equal to ortho-methylamino phenyl; further provided that when n=p=1, $X_2$=$CH_2$ and B'=adenosine, then $R_1$ and $R_2$ are not equal to napthylenylmethyl, napthylenylmethylene, or phenylmethylene.

Novel compounds of the present invention also include compounds of Formula Ia, wherein B and B' are independently pyrimidine (pyrimidine/pyrimidine dinucleotide), provided that when m+n+p=1, $R_{16}$=$CH_3$, and $R_5$ and $R_6$ are taken together as oxygen doubly bonded to C, then $R_7$ is not equal to $CH_3$ (Z' does not equal to acetate); also provided that when m+n+p=3, B and B'=uridine, and $R_5$ and $R^6$ are taken together as oxygen doubly bonded to C, then $R_7$ is not equal to phenyl for Y'=$OR_1$ and/or Y=$OR_4$ (Y and Y' does not equal to benzoyl); further provided that when m+n+p=1, then both $R_8$ and $R_9$ are not $CH_3$ (Z' and Y' taken together do not equal isopropylidine).

Novel compounds of the present invention also include compounds of Formula Ia, wherein B is a purine or residue according to general formula IV, and B' is a pyrimidine residue according to general formula V, (purine/pyrimidine dinucleotide); provided that Y' is not equal to $OCH_3$ when Z', Y, or Y'=H or OH; further provided that $R_9$ is not equal to $OCH_2CH_3$ when $R_9$=H(Z' and Y' or Z and Y taken together do not equal to an orthoethylester).

Novel compounds of the present invention also include compounds of Formula Ia, wherein B and B' are independently a purine residue according to general formula IV, (purine/purine dinonucleotide); provided that (a)Y or Y' is not equal to $OCH_3$ when $R_{10}$=$NH_2$ or 0; (b)$R_8$ is not equal to $OCH_3$ or $OCH_2CH_3$ when $R_9$=H; (c) both $R_8$ and $R_9$ are not equal to $CH_3$; (d) when m+n+p=1, then $R_8$ and $R_9$ does not equal $OCH_2CH_3$; (e) when $R_{10}$=$NH_2$, and when $R_5$ and $R^6$ are taken together as oxygen doubly bonded to C, then $R_7$ is not equal to ortho-methylaminophenyl; (f) when m+n+p=1, and when $R_5$ and $R_6$ are taken together as oxygen doubly bonded to C, then $R_7$ is not equal to $CH(CH_2CH_2SCH_3)NHS(o-NO_2-Ph)$ or $CH(CH_2Ph)NHS(o-NO_2-Ph)$.

Preferred compounds of the present invention include 2'- or 3'-phenylcarbamate UTP, 2',3'-di-phenylcarbamate UTP, 2',3'-phenylacetaldehyde acetal ADP, di[3'(phenylcarbamate)dUp2dU], 2',3'-phenylacetaldehyde acetal Up3U, di 2',3'-phenylacetaldehyde acetal Up3U, 2',3'-phenylacetaldehyde acetal Up4A, 2',3'-phenylacetaldehyde acetal Ap4U, di 2',3'-phenylacetaldehyde acetal Ap4U, 2',3'-phenylacetaldehyde acetal Ip4U, 2',3'-phenylacetaldehyde acetal Up4U, 2',3'-phenylacetaldehyde acetal Ip4U, 2',3'-phenylacetaldehyde acetal Up4dC, tetraphenylcarbamate Up4U, di2',3'-benzaldehyde acetal Ip4U, di 2',3'-benzaldehyde acetal Up4U, 2',3'-benzaldehyde acetal Up4U, di 2',3'-phenylacetaldehyde acetal Cp4U, 2',3'-phenylacetaldehyde acetal Cp4U, 2',3'-phenylacetaldehyde acetal Up4C, 2',3'-phenylacetaldehyde acetal Up4T, di 2',3'-benzaldehyde acetal Cp4U, 2',3'-benzaldehyde acetal Ip4U, 2',3'-benzaldehyde acetal Up4U, 2',3'-benzaldehyde acetal Up4dC, 2',3'-benzaldehyde acetal Cp4U, 2',3'-benzaldehyde acetal Up4C, 2',3'-phenylpropionaldehyde acetal Up4U, di 2',3'-phenylpropionaldehyde acetal Up4U, 2',3'-benzaldehyde acetal Cp4C, Bis MANT Up4U, Mant Up4U, Di 2',3'-benzylacetal Up4U, Mono 2', 3'-benzylacetal Up4U, Triphenyl carbamate Up4U, 2',3'-phenylcarbamate Up4U, and monophenylcarbamate Up4U.

Novel mononucleoside 5'-monophosphates compounds include compounds of Formula Ib':

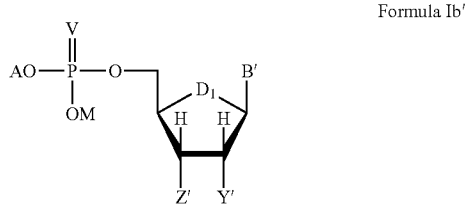

Formula Ib' wherein:
V=O;
A=M;
M=H or a pharmaceutically-acceptable inorganic or organic counterion;
$D_1$=O;
Y'=H, OH, or $OR_1$;
Z'=H, OH, or $OR_2$; with the proviso that at least one of Y' and Z' is OR$_1$ or OR$_2$;

$R_1$ and $R_2$ are residues which are linked directly to the 2' and/or 3' hydroxyls of the furanose or carbocycle via a carbon atom according to Formula II, or linked directly to two of the 2' and 3' hydroxyls of the furanose or carbocycle via a common carbon atom according to Formula III,

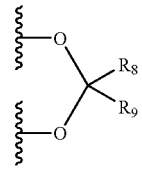

Formula III wherein:
the O atoms are the 2'- and 3'-oxygens of the furanose; and the 2'- and 3'-oxygens of the furanose are linked by a common carbon atom to form a cyclical acetal; and
$R_8$ is hydrogen; and
$R_9$ is selected from the group consisting of aralkyl, aryl, substituted aralkyl, and substituted aryl;
in which the aralkyl groups are straight chained from 1 to 5 carbons, with or without unsaturation and without heteroatoms in the alkyl portion, and are monocyclic moieties from 5 to 6 carbons in the aryl portion; and the aryl groups are monocyclic moieties from 4 to 6 carbons, with or without heteroatoms;
B' is a purine residue according to general Formula IV
wherein:
$R_{10}$ is acylamino, according to Formula VI; and
$R_{17}$ is amino or mono- or disubstituted amino such that the moiety according to Formula VI is a urea;
J=carbon;
$R_{11}$ is absent;
$R_{12}$ is hydrogen; and
$R_{13}$ is hydrogen.

For mononucleoside 5'-monophosphates, preferred compounds of the present invention include 2',3'-phenylacetaldehyde acetal-6-N-phenylurea AMP (compound 22), 2',3'-phenylacetaldehyde acetal-6-N-n-hexylurea AMP (compound 23), 2',3'-phenylacetaldehyde acetal-6-N-ethylurea AMP (compound 24), 2',3'-phenylacetaldehyde acetal-6-N-cyclopentylurea AMP (compound 25), 2',3'-cinnamyl acetal-6-N-n-hexylurea AMP (compound 26), 2',3'-cinnamyl acetal-6-N-ethylurea AMP (compound 27), 2',3'-cinnamyl acetal-6-N-phenylurea AMP (compound 28), 2',3'-cinnamyl acetal-6-N-n-propylurea AMP (compound 29), 2',3'-cinnamyl acetal-6-N-n-butylurea AMP (compound 30), 2',3'-phenylpropargyl acetal-6-N-phenylurea AMP (compound 31), 2',3'-phenylpropargyl acetal-6-N-n-hexylurea AMP (compound 32), 2',3'-phenylpropargyl acetal-6-N-n-butylurea AMP (compound 33), 2',3'-phenylpropargyl acetal-6-N-n-propylurea AMP (compound 34), 2',3'-phenylpropargyl acetal-6-N-ethylurea AMP (compound 35), 2',3'-benzaldehyde acetal-6-N-ethylurea AMP (compound 36), 2',3'-benzaldehyde acetal-6-N-n-propylurea AMP (compound 37), 2',3'-benzaldehyde acetal-6-N-n-butylurea AMP (compound 38), 2',3'-benzaldehyde acetal-6-N-n-hexylurea AMP (compound 39), and 2',3'-benzaldehyde acetal-6-N-cyclopentylurea AMP (compound 40).

Preferred compositions also comprise the following Compounds 1–40. In the following structures hydrogens which are understood to be present have been omitted for the sake of simplicity. Tautomers drawn represent all tautomers possible. As diastereomers are generated with the introduction of the acetal group, structures containing this moiety are taken to mean either of the possible diastereomers alone or a mixture of diasteromers in any ratio.

Compound 1

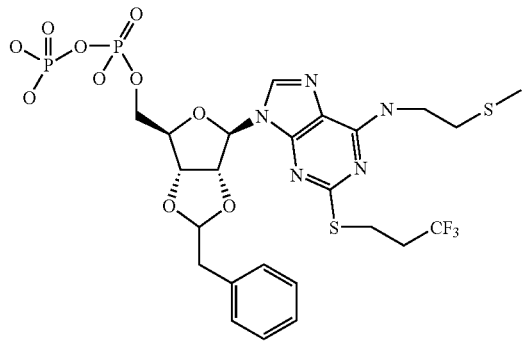

Compound 2

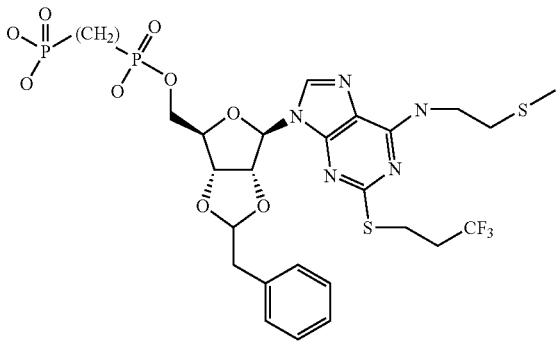

Compound 3

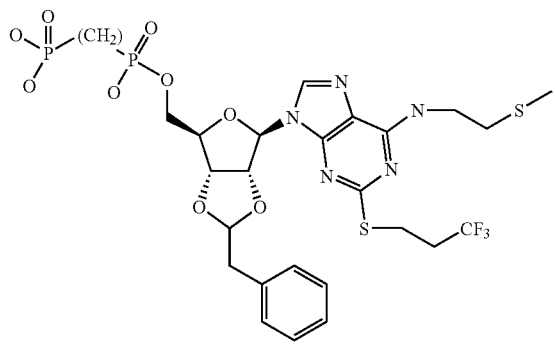

Compound 4

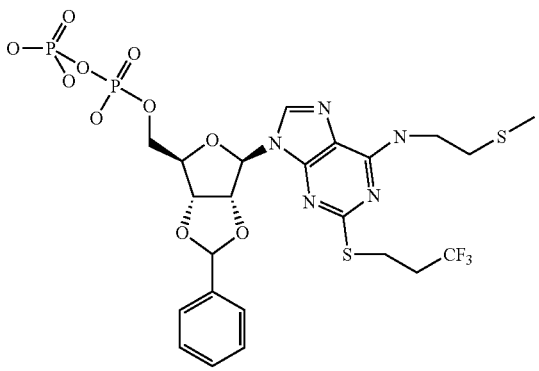

2-(3-trifluoromethylpropyl)thio-6-(2-methylthio) ethylamino-2′,3′-(benzyl)methylenedioxy purine riboside 5′–α,β–difluoromethylene diphosphate Compound 5

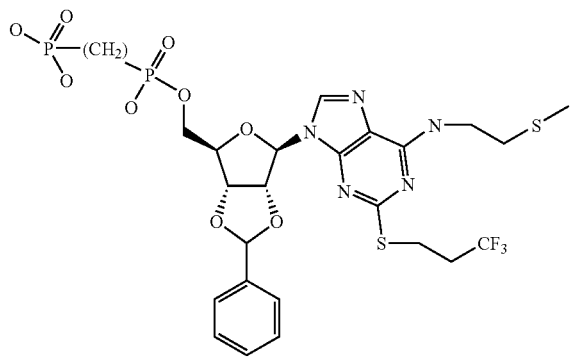

Compound 6

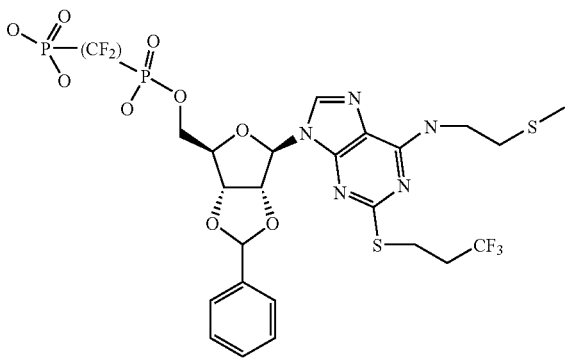

Compound 7
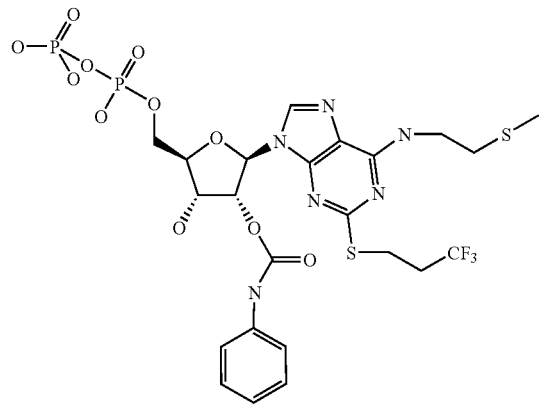
Compound 8
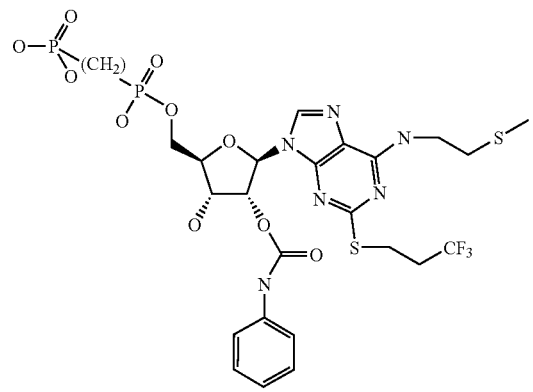
Compound 9
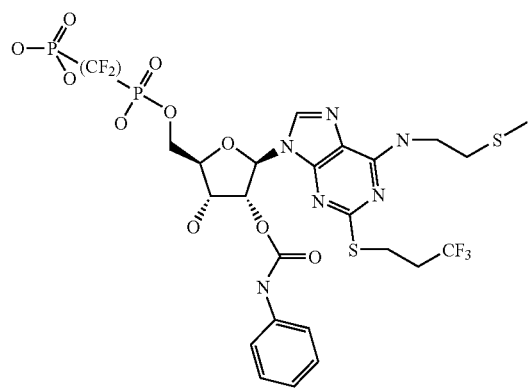
Compound 10
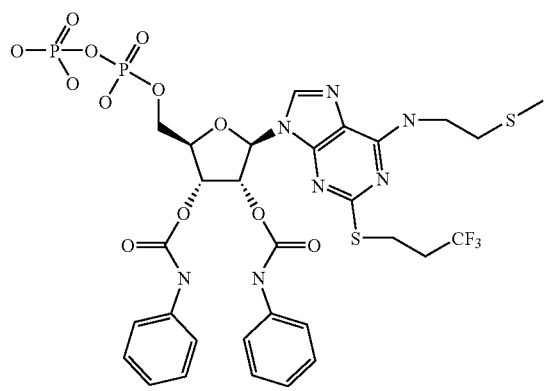
Compound 11
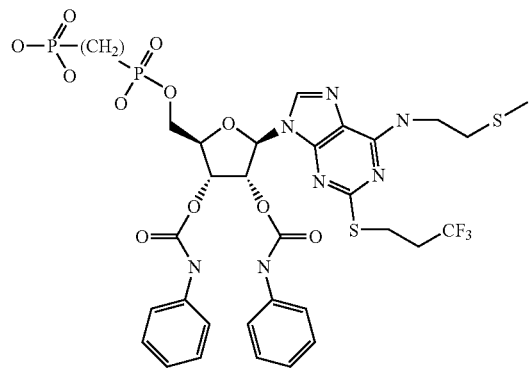
Compound 12
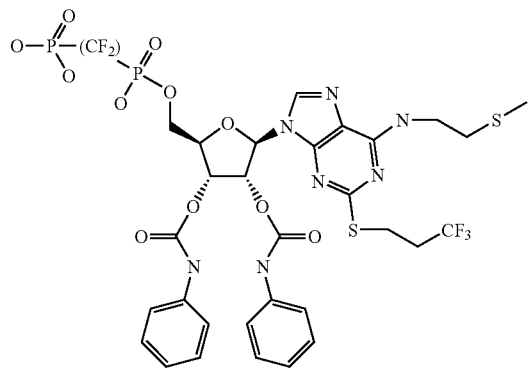

-continued
Compound 13
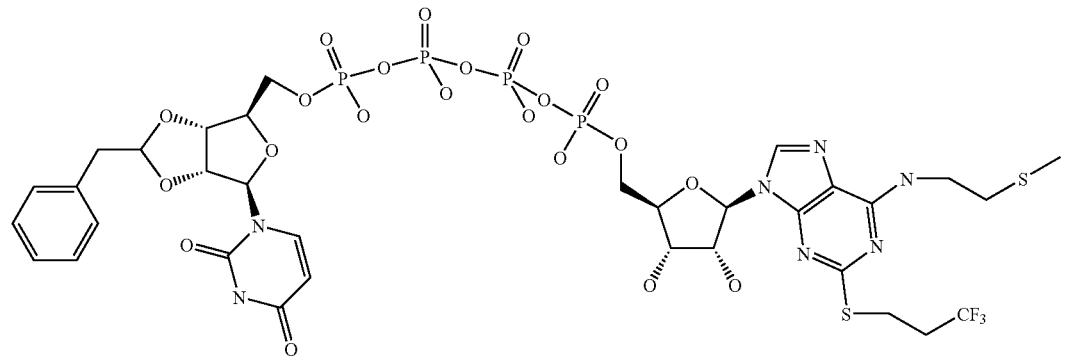
Compound 14
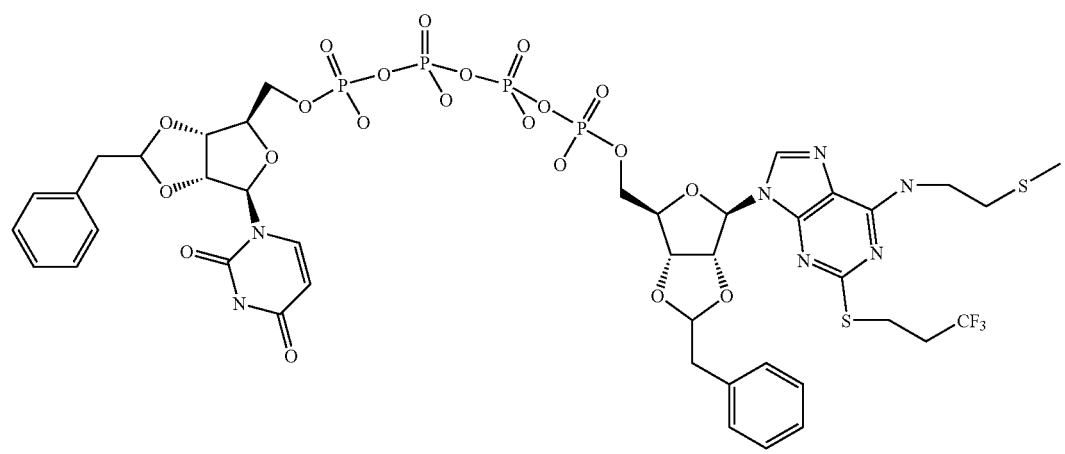
Compound 15
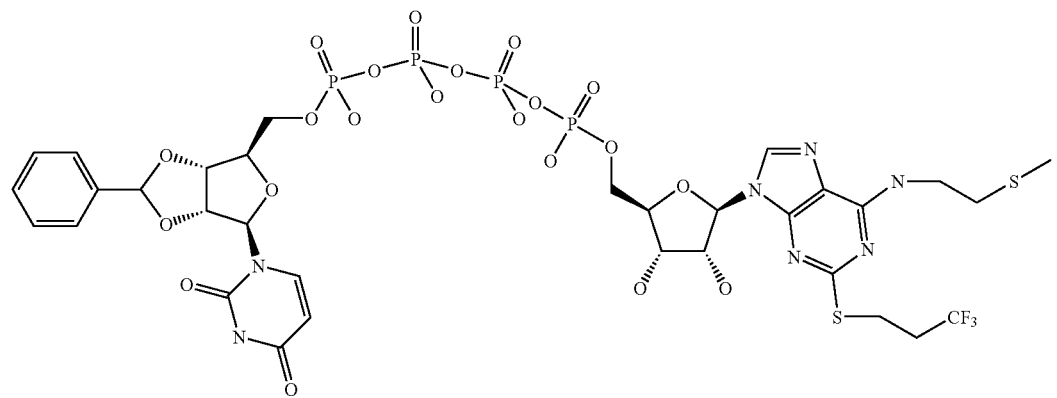
P$^1$-[2-(3-trifluoromethylpropyl)thio-6-(2-methylthio)ethylamino 2′,3′-(benzyl)methylene dioxy purine riboside]-P$^4$-(2′,3′-(benzyl)methylene dioxy uridine) tetraphosphate -continued
Compound 16
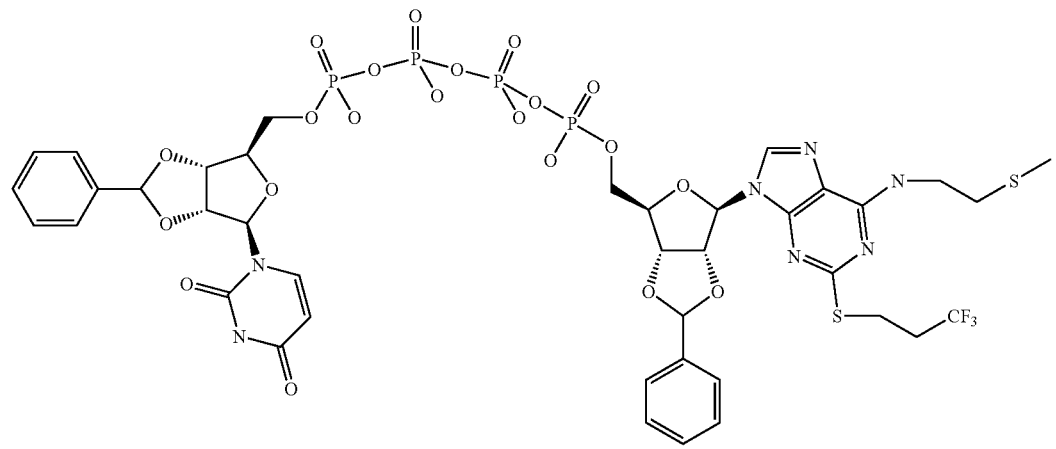
Compound 17
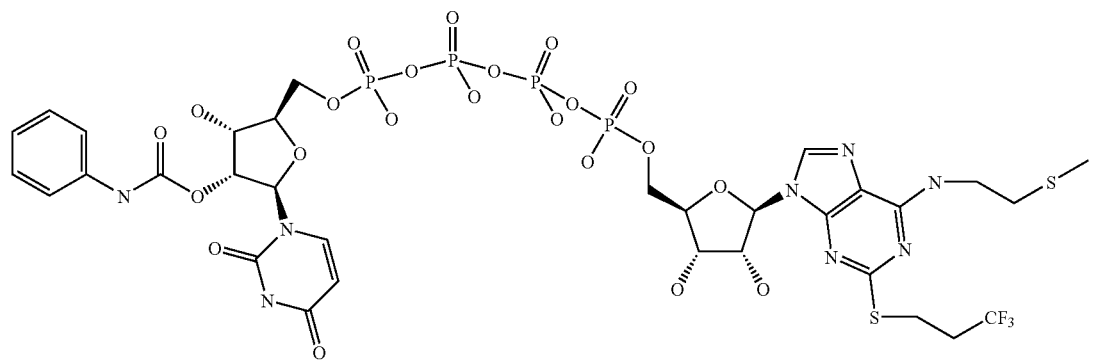
Compound 18
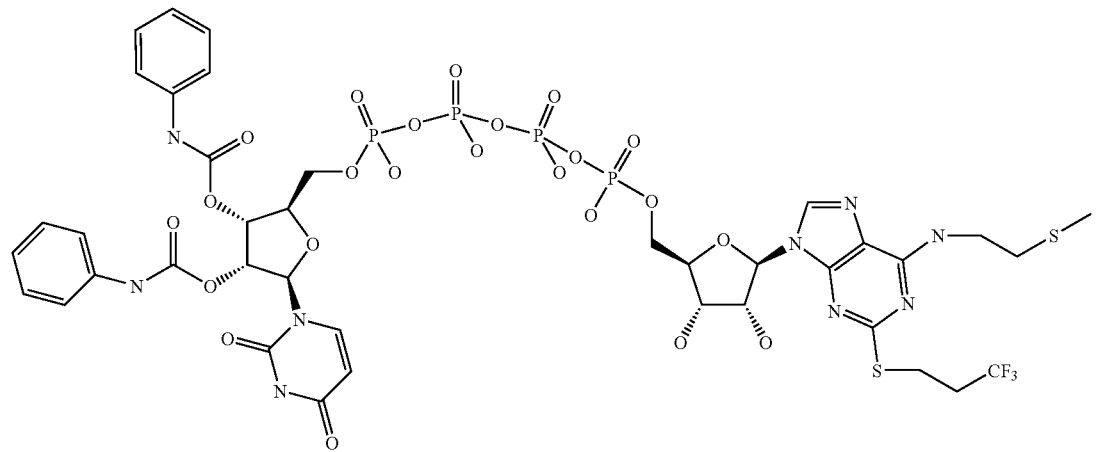

Compound 19
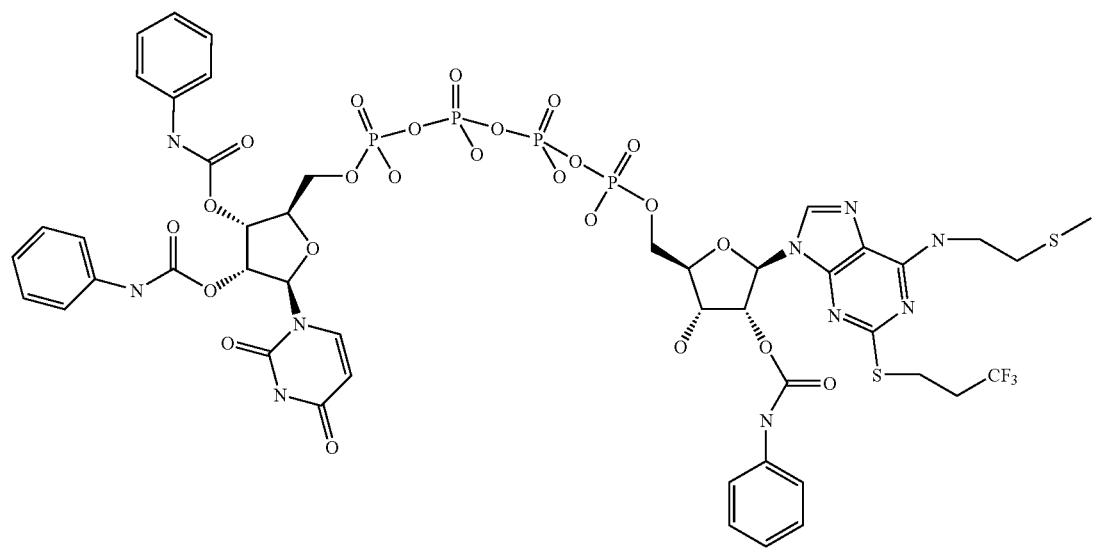
Compound 20
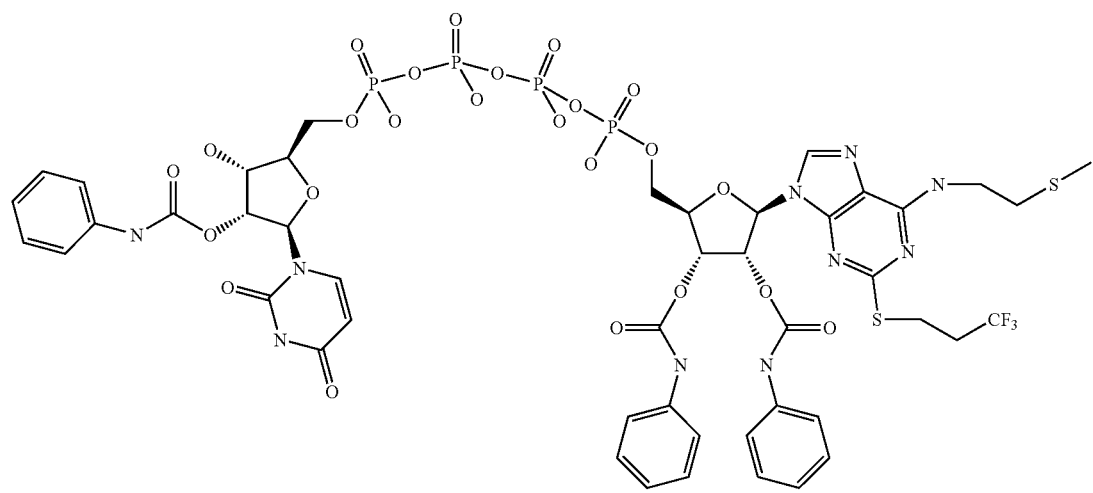
Compound 21
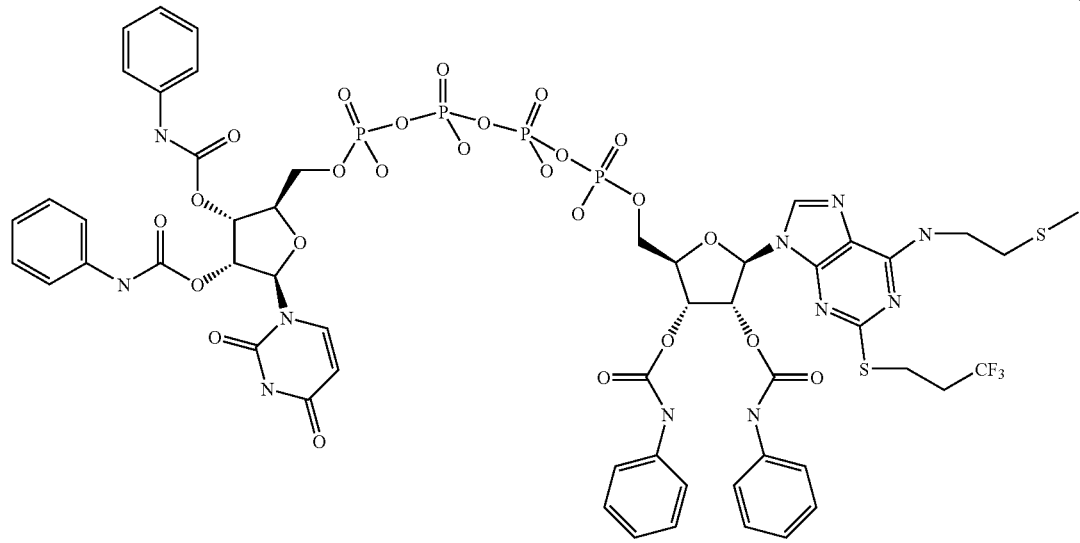

-continued
Compound 22
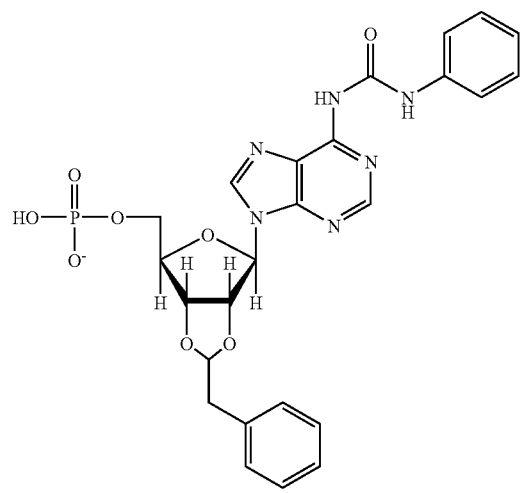
Compound 23
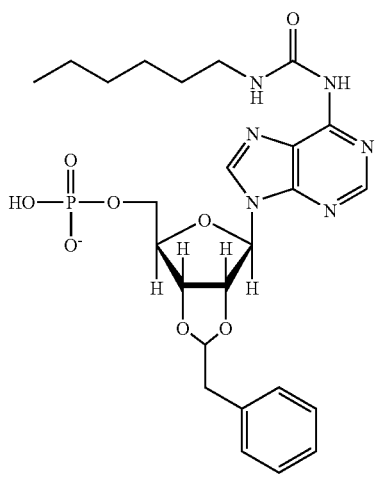
Compound 24
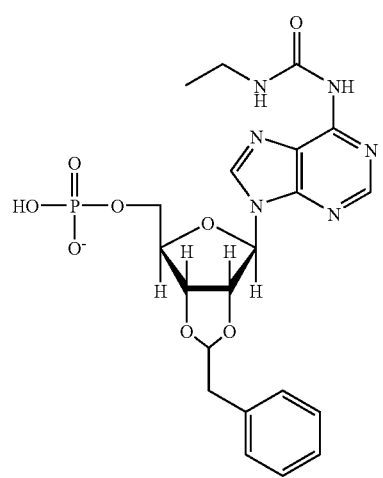
Compound 25
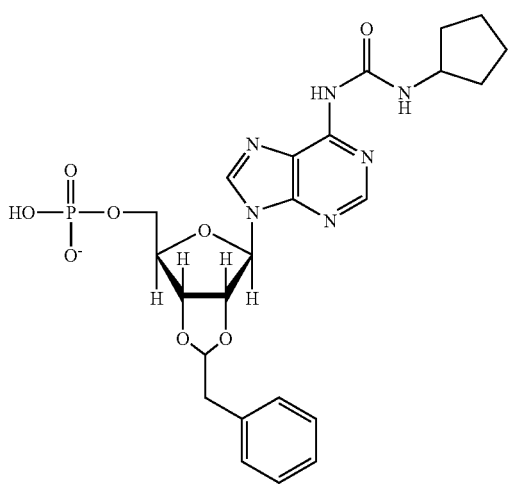
Compound 26
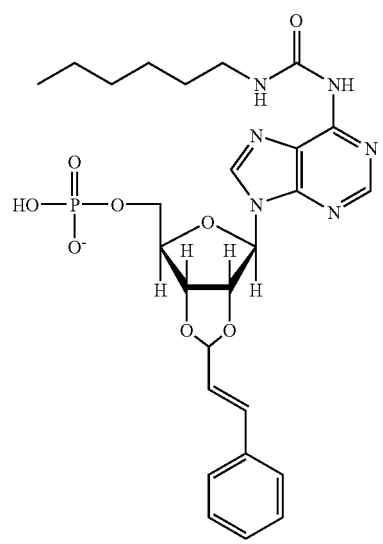
Compound 27
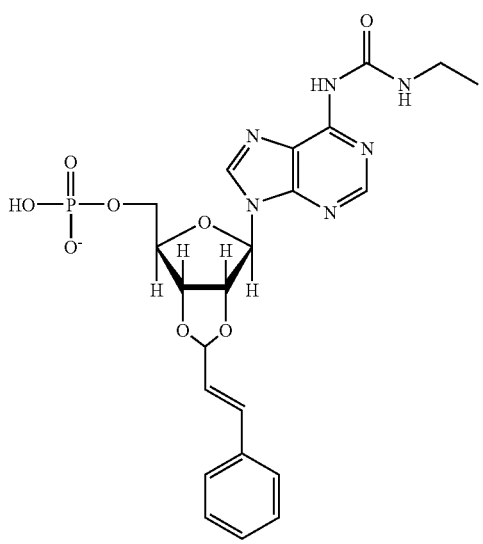

Compound 28
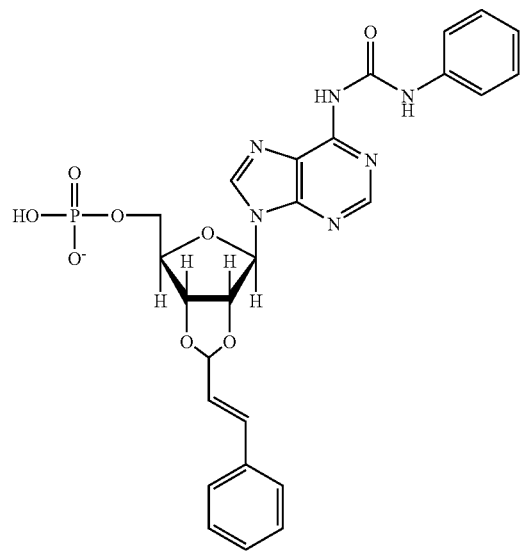
Compound 29
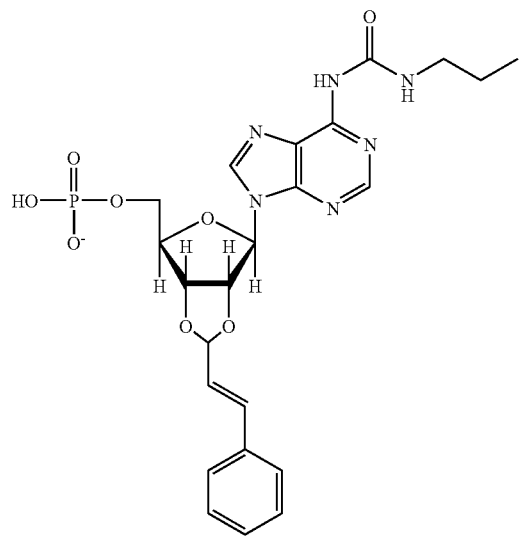
Compound 30
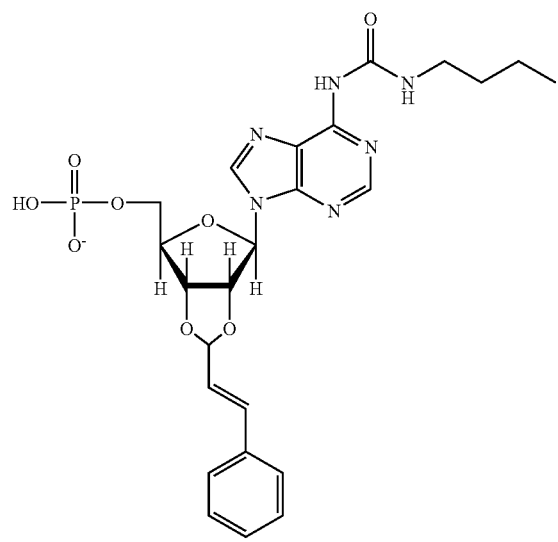
Compound 31
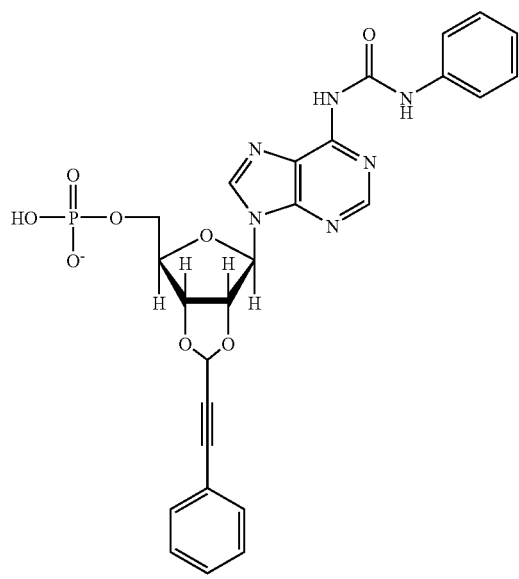

Compound 32
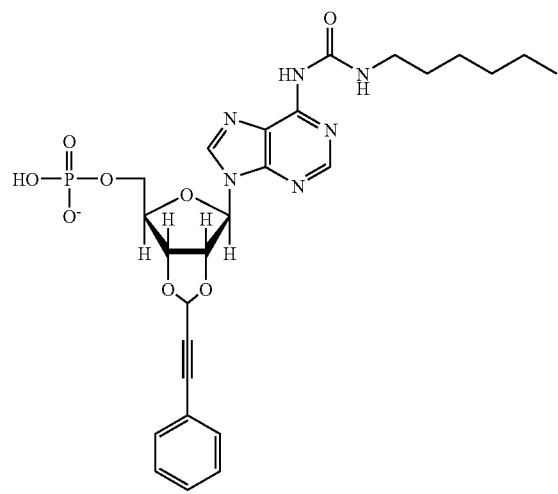
Compound 33
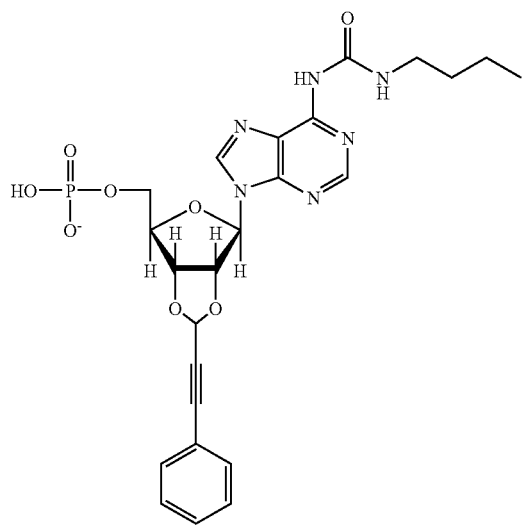
Compound 34
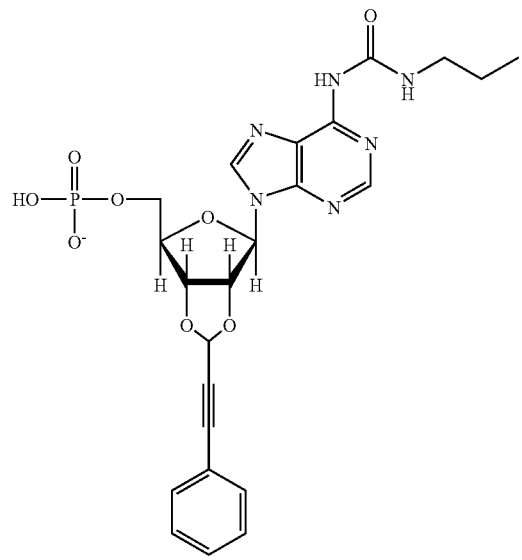
Compound 35
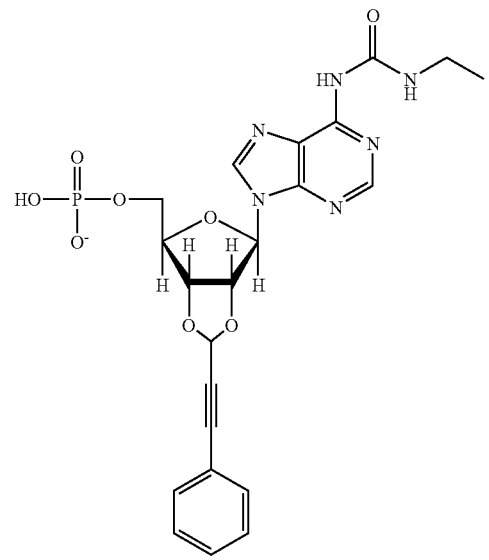

-continued
Compound 36
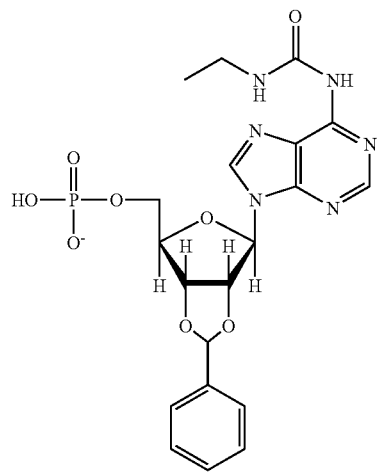
Compound 37
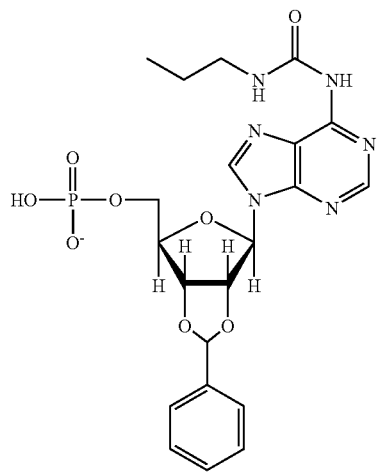
Compound 38
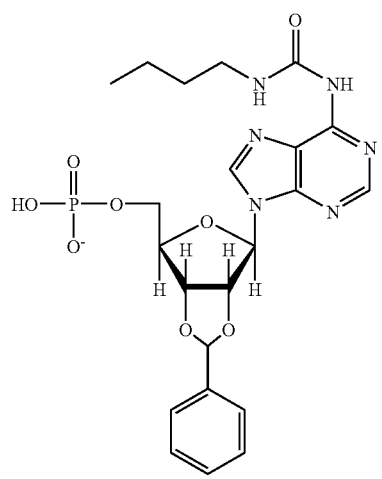
Compound 39
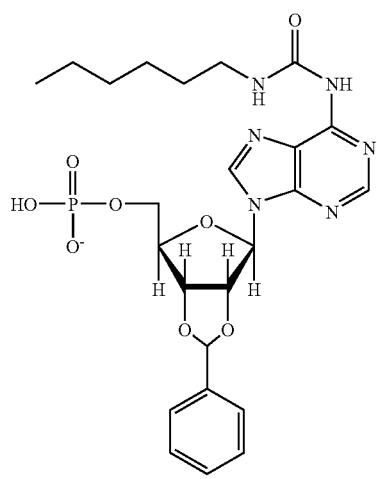
Compound 40
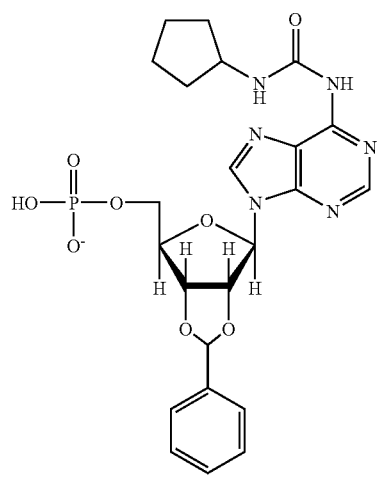

The invention is illustrated further by the following examples that are not to be construed as limiting the invention in scope to the specific procedures described in them.

EXAMPLES

Example 1

2'(3')-O-((phenylaminocarbonyl)-uridine 5'-)triphosphate

Uridine 5'-triphosphate, ditributylammonium salt (100 mg, 0.176 mmol; prepared from the trisodium salt by treatment with Dowex 50W×4H$^+$ in water, followed by mixing the protonated species with an excess of tributylamine, stripping and lyophilization) was dissolved in dry DMF (1 mL) and phenylisocyanate (19 µL, 0.176 mmol) added. The reaction mixture was heated at 45° C. for 15 minutes, at which point a further portion of phenylisocyanate (19 µL, 0.176 mmol) was added. The solution was heated at 45° C. overnight and the DMF was removed on a rotary evaporator. The residual oil was partitioned between water (2 mL) and ethyl acetate (2 mL) and the layers were separated. The aqueous layer was extracted twice more with ethyl acetate (2 mL each) and the water was removed on a rotary evaporator. The residue was dissolved in water (1.5 mL) and the product isolated by repeated injections onto a preparative HPLC column (Alltech Nucleotide/Nucleoside C18, 7 um, 10×250 mm, gradient from 0.1 M ammonium acetate to methanol over 30 minutes, 5 mL/min, monitor at 260 nm). The yield of the carbamate was 26 mg (22%, calculated for the tetraammonium salt). 1H NMR showed the product to be a mixture of 2' and 3' carbamates. The product so obtained can be used for the purposes of this invention per se or can be activated with a suitable coupling agent (e.g. a carbodiimide) and reacted with a variety of nucleotides to generate novel dinucleoside polyphosphates.

1H NMR (D20, 300 MHz): δ 4.10–4.47 (m, 4H), 5.17 (m, 1H), 5.83 (dd, 1H), 5.96 (m, 1H), 7.04 (t, 1H), 7.25 (m, 4H), 7.79 (m, 1H). $^{31}$P NMR (D2O, 121.47 MHz): δ –9.54 (m, 1P), –10.20 (m, 1P), –21.87 (m, 1P).

Example 2

2'(3')-O-(phenylaminocarbonyl)-P$^1$,P$^4$-di(uridine 5'-)tetraphosphate ["monophenylcarbamate Up4U"], Di-2'(3')-O-(phenylaminocarbonyl)-P$^1$,P$^4$-di(uridine 5'-)tetraphosphate ["diphenylcarbamate Up4U"] and Tri-2'(3')-O-(phenylaminocarbonyl)-P$^1$,P$^4$-di(uridine 5'-)tetraphosphate ["triphenylcarbamate Up4U"]

P$^1$,P$^4$-Di(uridine 5'-)tetraphosphate, ditributylammonium salt (211 mg, 0.182 mmol; prepared from the tetrasodium salt by treatment with Dowex 50W×4H$^+$ in water, followed by mixing the protonated species with an excess of tributylamine, stripping and lyophilization) was dissolved in dry DMF (2 mL) and phenylisocyanate (40 µL, 3.64 mmol) added in a single portion. The homogeneous reaction mixture was heated overnight at 45° C., whereupon TLC (silica gel, 50% isopropanol/50% ammonium hydroxide) indicated a substantial conversion to two products. The solvent was removed on a rotary evaporator and the residue was partitioned between water (7 mL) and ethyl acetate (10 mL). The layers were separated, and the aqueous was extracted twice more with ethyl acetate. (10 mL each). The water was removed from the aqueous extract and the residual oil lyophilized overnight. The solid obtained was reconstituted in water (3 mL) and the two products separated by repeated injections onto a semipreparative HPLC column (Alltech Nucleotide/Nucleoside C18, 7 um, 10×250 mm, gradient from 0.1 M ammonium acetate to methanol over 30 minutes, 5 mL/min, monitor at 260 nm). Stripping and lyophilization gave the mono-phenylcarbamate (48 mg, 27% yield), di-phenylcarbamate (16 mg, 8% yield) and a trace amount of the triphenylcarbamate, as the tetraammonium salts. All three products were mixtures of the corresponding 2'/3' regiosiomers.

Monophenylcarbamate: $^1$H NMR (D20, 300 MHz): δ 4.08–4.65 (m, 9H), 5.14 (d, 1H), 5.75–5.94 (m, 4H), 7.01 (t, 1H), 7.22 (m, 4H), 7.76 (m, 2H). $^{31}$P NMR (D$_2$O, 121.47 MHz): δ –10.17 (m, 2P), –21.81 (m, 2P).

Diphenylcarbamate: $^1$H NMR (D$_2$O, 300 MHz): δ 4.13–4.43 (m, 8H), 5.12 (m, 2H), 5.84 (m, 4H), 7.01 (m, 2H), 7.21 (m, 8H), 7.75 (dd, 2H). $^{31}$P NMR (D$_2$O, 121.47 MHz): δ –10.19 (m, 2P), –21.65 (m, 2P).

Triphenylcarbamate: $^1$H NMR (D$_2$O, 300 MHz): δ 4.29 (m, 7H), 4.5.10 (m, 1H), 5.27 (m, 2H), 5.87 (m, 4H), 7.09 (m, 15H), 7.76 (d, 2H). $^{31}$P NMR (D$_2$O, 121.47 MHz): δ –10.30 (m, 2P), –21.73 (m, 2P).

Example 3

P$^1$,P$^4$-Tetra-(2'(3')-O-(phenylaminocarbonyl) di(uridine 5'-)tetraphosphate [tetraphenylcarbamate Up4U"]

This derivative was prepared according to the method of example 2. P$^1$,P$^4$-Di(uridine 5'-)tetraphosphate, ditributylammonium salt (200 mg, 0.172 mmol) was treated with 16 eq of phenylisocyanate (300 uL, 2.76 mmol) in DMF and stirred overnight at 35° C. The solvent was evaporated and the excess reagents removed by extraction of an aqueous solution of the product with ethyl acetate. Following preparative HPLC as previously described, 93 mg (30% yield) of the tetraphenylcarbamate was obtained.

Tetraphenylcarbamate: $^1$H NMR (D$_2$O, 300 MHz): δ 7.75 (d, 2H), 7.11 (m, 16H), 6.94 (m, 4H), 5.95 (d, 2H), 5.80 (d, 2H), 5.32 (m, 2H), 5.23 (m, 2H), 4.42 (m, 2H), 4.16 (m, 2H). $^{31}$P NMR (D$_2$O, 121.47 MHz): ): δ –10.30 (m, 2P), –22.32 (m, 2P).

Example 4

2',3'-(benzyl)methylenedioxy-P$^1$,P$^4$-di(uridine 5'-) tetraphosphate ["Mono 2'/3' benzylacetal Up4U"] and P$^1$,P$^4$-Di-(2',3'-((benzyl)methylenedioxy) di(uridine 5'-)tetraphosphate ["Di 2'/3' benzylacetal Up4U"]

P$^1$,P$^4$-Di(uridine 5'-)tetraphosphate, tetrasodium salt (290 mg, 0.332 mmol) was dissolved in 98% formic acid and phenylacetaldehyde, dimethyl acetal (110 uL, 0.662 mmol) added. The reaction was stirred at ambient temperature for 3 days, at which point TLC (silica gel, 50% isopropanol/ 50% ammonium hydroxide) and HPLC (C18) showed good conversion to two less polar products. The formic acid was removed on a rotary evaporator, and the residue partitioned between 0.7 M ammonium bicarbonate (15 mL) and butyl acetate (15 mL). The layers were separated and the aqueous was washed with a further portion of butyl acetate (10 mL). The aqueous layer was stripped and the residue lyophilized overnight. The crude product was dissolved in water (5 mL) and the components separated by preparative HPLC (Waters Novapak C18, 6 um, 25×100 mm, gradient from 0.1 M ammonium acetate to methanol over 30 minutes, 30 mL/min, monitor at 260 nm). The yield of the monoacetal was 88 mg (28%) and of the diacetal 60 mg (17%), both as the tetraammonium salts.

Monoacetal: $^1$H NMR (D$_2$O, 300 MHz): δ 2.99 (d, 2H), 4.01–4.32 (m, 8H), 4.77 (m, 5.33 (m, 2H), 5.74 (d, 1H), 5.81 (m, 2H), 7.21 (m, 5H), 7.64 (d, 1H), 7.79 (d, 1H). $^{31}$P NMR (D$_2$O, 121.47 MHz): δ −10.18 (m, 1P), −10.78 (m, 1P), −22.00 (m, 2P).

Diacetal: $^1$H NMR (D$_2$O, 300 MHz): δ 2.98 (d, 4H), 3.99 (m, 4H), 4.27 (m, 2H), 2H), 5.36 (m, 2H), 5.73 (d, J=8.1 Hz, 2H), 7.21 (m, 10H), 7.61 (d, J=8.1 Hz, 2H). $^{31}$P NMR (D$_2$O, 121.47 MHz): δ −10.57 (m, 2P), −21.81 (m, 2P).

Example 5

2',3'-((benzyl)methylenedioxy) P$^1$,P$^3$-uridine 5'-)triphosphate ["2'3' phenylacetaldehyde acetal Up3U"] and P$^1$,P$^3$-Di-(2',3'-((benzyl)methylenedioxy) uridine 5'-)triphosphate ["di 2'3' phenylacetaldehyde acetal Up3U"]

P$^1$,P$^3$-Di(uridine 5'-)triphosphate, trisodium salt (100 mg, 0.129 mmol) was dissolved in 98% formic acid and phenylacetaldehyde, dimethyl acetal (64 uL, 0.386 mmol) added. After overnight stirring at room temperature, the formic acid was removed, and the residue partitioned between 1 M sodium bicarbonate and ethyl acetate. Following removal of the organic layer, the product was purified on preparative HPLC, as previously described. Following lyophilization, 40 mg (36%) of the monoacetal and 24 mg (19%) of the diacetal were obtained.

Monoacetal: $^1$H NMR (D$_2$O, 300 MHz): δ 7.7s (d, 2H), 7.54 (d, 2H), 7.16 (s, 5H), 3H), 5.31 (s, 1H), 5.23 (s, 1H), 4.66 (m, 2H), 4.10 (m, 8H), 2.93 (d, 2H). $^{31}$P NMR (D$_2$O, 121.47 MHz): δ −10.30 (m, 1P), 10.81 (m, 1P), −21.99 (m, 1P).

Diacetal: $^1$H NMR (D$_2$O, 300 MHz): δ 7.51 (d, 2H), 7.15 (m, 10H), 5.65 (d, 2H), 5.31 (d, 2H), 5.20 (t, 2H), 4.63 (m, 2H), 4.13 (m, 2H), 3.88 (m, 4H), 2.90 (d, 4H). $^{31}$P NMR (D$_2$O, 121.47 MHz): δ −10.75 (m, 2P), −21.97 (m, 1P).

Example 6

P$^1$-2',3'-((benzyl)methylenedioxy) (uridine 5'-) P$^4$-(deoxycytidine 5'-)tetraphosphate ["2'3' phenylacetadehyde acetal Up4dC"]

P$^1$-(uridine 5'-) P$^4$-(deoxycytidine 5'-)tetraphosphate, tetrasodium salt (100 mg, 0.16 mmol) was dissolved in 98% formic acid (1 mL), and phenylacetaldehyde, dimethyl acetal (57 uL, 0.384 mmol) added. After overnight stirring, the formic acid was removed and the residue partitioned between 1 M sodium bicarbonate and ethyl acetate. After separation of the layers, the product was purified on preparative HPLC, as previously described. Yield 40 mg (36%). This product was amenable to subsequent modification of the deoxy cytidine base by the procedures described in examples 9-13, giving rise to lipophilic bifunctional molecules falling within the scope of this invention.

Monoacetal: $^1$H NMR (D$_2$O, 300 MHz): δ 7.98 (d, 1H), 7.62 (d, 1H), 7.21 (m, 5H), 2H), 5.74 (d, 1H), 5.39 (d, 1H), 5.31 (t, 1H), 4.77 (m, 2H), 4.45 (m, 1H), 4.03 (m, 5H), 2.99 (d, 2H), 2.29 and 2.21 (M, 2H). $^{31}$P NMR (D$_2$O, 121.47 MHz): δ −10.15 (m, 1P), −10.68 (m, 1P), −21.98 (m, 2P).

Example 7

3'-O-(phenylaminocarbonyl)-2'-deoxy(uridine 5')-monophosphate

Deoxyuridine 5'-monophosphate, tetrabutylammonium salt (135 mg, 0.274 mmol; prepared from the disodium salt by treatment with Dowex 50W×4H$^+$, followed by stirring the resultant neutral species with excess tributylamine, stripping and lyophilization) was dissolved in dry DMF (1 mL). Phenylisocyanate (60 uL, 0.547 mmol) was added and the mixture heated overnight at 45° C., at which time TLC (silica gel, 50% isopropanol/50% ammonium hydroxide) and HPLC (C 18) indicated a substantial conversion to a less polar product. The DMF was stripped on a rotary evaporator and the oily residue partitioned between water (10 mL) and ethyl acetate (10 mL). The layers were separated and the aqueous layer was rewashed with ethyl acetate (2×10 mL). The water was removed and the residue was dissolved in water (2 mL). The product was isolated by repeated injections onto semipreparative HPLC (Alltech Nucleotide/Nucleoside C18, 7 um, 10×250 mm, gradient from 0.1 M ammonium acetate to methanol over 30 minutes, 5 mL/min, monitor at 260 nm). The yield was 67 mg as the diammonium salt (53%).

$^1$H NMR (D$_2$O, 300 MHz): δ 2.21 (m, 2H), 3.84 (s, 2H), 4.13 (s, 1H), 5.08 (d, 1H), 5.63 (d, 1H), 6.06 (t, 1H), 6.89 (br. t, 1H), 7.10 (m, 4H), 7.72 (d, 1H). $^{31}$P NMR (D$_2$O, 121.47 MHz): δ−2.31 (s).

P$^1$-(3'-O-(phenylaminocarbonyl)-2'-deoxyuridine 5'-)P$^4$-(uridine 5'-)tetraphosphate Uridine 5'-triphosphate, ditributylammonium salt (prepared from the trisodium salt by treatment with Dowex 50 W×4H$^+$, followed by stirring the resultant neutral species with excess tributylamine, stripping and lyophilization) is treated with 1.5 equivalents of dicyclohexylcarbodiimide in DMF for 2 hours at room temperature. The dicyclohexylurea is filtered off, and the resultant uridine 5'-cyclical triphosphate is treated with 3'-O-(phenylaminocarbonyl)-2'-deoxy (uridine 5')-monophosphate, which is in the monotributylammonium salt form. The reaction mixture is stirred for several days at 45° C., and the solvent is removed. The products are separated by preparative HPLC, as has been previously described.

Example 8

2'(3')-(2-methylamino)benzoyl-P$^1$,P$^4$-di(uridine 5'-)tetraphosphate ("MANT Up4U") and P$^1$,P$^4$-Di-(2' (3')-(2-methylamino)benzoyl uridine 5'-)tetraphosphate ("Bis MANT Up4U")

P$^1$,P$^4$-Di(uridine 5'-)tetraphosphate, tetrasodium salt (800 mg, 0.93 mmol) was dissolved in water (5 mL) and the pH adjusted to 7.6 by the addition of solid sodium bicarbonate. N,N-dimethylformamide(DMF, 5 mL) was added, followed by N-methylisatoic anhydride (231 mg, 1.3 mmol) and the suspension was heated at 50° C. for 2.5 hrs. TLC (silica gel, 50% isopropanol, 50% ammonium hydroxide) indicated that the reaction was not done by this time, so a further portion of N-methylisatoic anhydride (100 mg, 0.56 mmol) was added and the reaction heated for another hour. The DMF was removed on a rotary evaporator and the residue was dissolved in a minimum of water and applied to a DEAE Sephadex A-25 column (3×60 cm). The column was eluted with a stepwise gradient from water to 1 M ammonium bicarbonate and the eluent monitored with a UV detector set at 254 nm. The two products that eluted were collected separately and the solvent was removed from each and the residue lyophilized overnight. $^1$H NMR indicated that the first product to elute was the monoacylated compound, while the latter was the diacylated derivative, and that both were mixtures with the acylation at either the 2' or 3' hydroxyls, but without two carbamates on the same sugar. The yield of the monoaminobenzoylated product was 150 mg (16%); the yield of the diaminobenzoylated compound was 91 mg (8.7%).

Monoaminobenzoylated derivative: $^1$H NMR (D$_2$O, 300 MHz): δ 2.70 (s, 3H), 4.09–4.55(m, 9H), 5.34 (m, 1H), 5.71 (m, 2H), 5.83 (dd, 1H), 6.01 (m, 1H), 6.57 (m, 1H), 6.65 (m, 1H), 7.25 (t, 1H), 7.72 (d, 2H), 7.81 (m, 2H). $^{31}$P NMR (D$_2$O, 121.47 MHz): δ −10.20 (m, 2P),−21.83 (m, 2P).

Diaminobenzoylated derivative: $^1$H NMR (D$_2$O, 300 MHz): δ 2.69 (s, 6H), 4.15–4.51 (m, 8H), 5.27 (m, 2H), 5.86 (m, 4H), 6.60 (m, 4H), 7.30 (m, 2H), 7.79 (m, 4H). $^{31}$P NMR (D$_2$O, 121.47 MHz): δ −10.16 (m, 2P), −21.76 (m, 2P).

Example 9

P$^1$-(4-N-(4-methoxyphenyl)aminocarbonylcytidine 5'-)-P$^4$-(uridine 5'-)tetraphosphate P$^1$-(cytidine 5'-)-P$^4$-(uridine 5'-)tetraphosphate, ditributylammonium salt (50 mg, 0.043 mmol; prepared from the tetraammonium salt by treatment with Dowex 50W×4H$^+$ in water, followed by mixing the protonated species with an excess of tributylamine in methanol, stripping and lyophilization) was dissolved in dry DMF (1 mL) and tributylamine (10 uL, 0.43 mmol), and p-methoxyphenylisocyanate (8.4 uL, 0.648 mmol) were added in a single portion. The homogeneous reaction mixture was heated overnight at 35° C., whereupon TLC (silica gel, 50% isopropanol/50% ammonium hydroxide) and HPLC (C18) indicated a substantial conversion to a single product. The solvent was removed on a rotary evaporator and the residue dissolved in water (1 mL). The product was isolated by repeated injections onto a semi-preparative HPLC column (Alltech Nucleotide/Nucleoside C18, 7 um, 10×250 mm, gradient from 0.1 M ammonium acetate to methanol over 30 minutes, 5 mL/min, monitor at 260 nm). Stripping and lyophilization gave the p-methoxyphenylurea (24 mg, 55% yield), as the tetraammonium salt.

The product so obtained can be derivatized on the 2' and/or 3' hydroxyl groups according to the foregoing methods (e.g. Examples 2–6).

$^1$H NMR (D$_2$O, 300 MHz): δ 3.59 (s, 3H), 4.01–4.20 (m, 10H), 5.68 (m, 3H), 6.71 (d, 2H), 7.18 (d, 2H), 7.67 (d, 1H), 8.06 (d, 1H). $^{31}$P NMR (D$_2$O, 121.47 MHz ): δ −10.13 (m, 2P), −21.76 (m, 2P).

Example 10

P$^1$-((4-bromophenyl)ethenocytidine 5'-)-P$^4$-(uridine 5'-)tetraphosphate

P$^1$-(cytidine 5'-)-P$^4$-(uridine 5'-)tetraphosphate, tetrasodium salt (500 mg, 0.57 mmol) was dissolved in water (5 mL) and a solution of 2,4'-dibromoacetophenone (792 mg, 2.85 mmol) in DMF (15 mL) added. The mixture was heated overnight at 40° C., and a further portion of the dibromoketone (400 mg, 1.44 mmol) in DMF (5 mL) added. The reaction was heated a further 5 hrs, and the solvents removed by evaporation. The residue was partitioned between water (20 mL) and ethyl acetate (25 mL) and the layers separated. The aqueous layer was washed with further ethyl acetate (2×15 mL) and the aqueous evaporated to dryness. The residue was dissolved in water (5 mL) and the product was isolated by repeated injections onto a semi-preparative HPLC column (see example 6 for conditions). The yield of the pure etheno compound was 80 mg (13.5%)

$^1$H NMR (D$_2$O, 300 MHz): δ 4.06 (m, 8H), 4.36 (m, 2H), 5.64 (dd, 2H), 6.07 (d, 1H), 7.45 (d, 2H), 7.54 (d, 2H), 7.59 (d, 1H), 7.63 (d, 1H), 7.93 (s, 1H). $^{31}$P NMR (D$_2$O, 121.47 MHz): δ −10.09 (m, 2P), −21.59 (m, 2P).

Example 11

P$^1$-((4-bromophenyl)etheno-2'-deoxycytidine 5'-)-P$^4$-(uridine 5'-)tetraphosphate Example 11 product was prepared from 100 mg P$^1$-(2'-deoxycytidine 5'-)-P$^4$-(uridine 5'-)tetraphosphate, tetrasodium salt and 2,4'-dibromoacetophenone, according to the general method of example 10. Yield=35 mg (30%).

$^1$H NMR (D$_2$O, 300 MHz): δ 2.31 (m, 2H), 4.03 (m, 8H), 5.60 (dd, 2H), 6.41 (d, 1H), 7.53 (m, 5H), 7.65 (d, 1H), 7.93 (s, 1H). $^{31}$P NMR (D$_2$O, 121.47 MHz): β −10.11 (m, 2P), −21.58 (m, 2P).

Example 12

P$^1$, P$^4$-Di((4-bromophenyl)ethenocytidine 5'-)-tetraphosphate

Example 12 product was prepared from 50 mg P$^1$,P$^4$-Di (cytidine 5'-)tetraphosphate, tetrasodium salt and 2,4'-dibromoacetophenone, according to the general method of example 10. Yield=20 mg (29%).

$^1$H NMR (D20, 300 MHz): δ 4.24 (m, 10H), 5.98 (d, 2H), 6.39 (d, 2H), 7.14 (m, 8H), 7.45 (m, 4H).). $^{31}$P NMR (D$_2$O, 121.47 MHz): δ −10.13 (m, 2P), −21.68 (m, 2P).

Example 13

P$^1$-((4-phenylphenyl)ethenocytidine 5'-)-P$^4$-(cytidine 5'-)tetraphosphate

Example 13 product was prepared from 50 mg P$^1$,P$^4$-Di (cytidine 5'-)tetraphosphate, tetrasodium salt and 2-bromo-4'-phenylacetophenone, according to the general method of example 10. Yield=15 mg (13%).

$^1$H NMR (D20, 300 MHz): δ 4.10 (m, 1OH), 5.48 (d, 1H), 5.87 (m, 2H), 6.68 (d, 1H), 7.20 (m, 3H), 7.36 (m, 6H), 7.68 (m, 3H). $^{31}$P NMR (D$_2$O, 121.47 MHz): δ 10.08 (m, 2P), −21.78 (m, 2P).

The products of examples 11–13 can be further derivatized according to the methods of Examples 1–8, to give bifunctional molecules that fall within the scope of the invention.

Example 14

2',3'-phenylacetaldehyde acetal adenosine 5'-monophosphate

Adenosine 5'-monophosphate, free acid (10.0 g, 28.8 mmol) was dissolved in trifluoroacetic acid (50 mL) and phenylacetaldehyde, dimethylacetal (18.50 mL, 121 mmol) added. The reaction was stirred at ambient temperature for 3 hours, after which the trifluoroacetic acid was evaporated and the residue partitioned between 1 M sodium bicarbonate (80 mL) and ethyl acetate (40 mL). The layers were separated, and the product was isolated from the aqueous layer via $C_{18}$ preparative HPLC. Yield=7.50 g (59%). The ammonium salt so obtained was converted to the mono-tributylammonium salt via treatment with a slight excess of tributylamine in aqueous N,N-dimethylformamide, followed by evaporation and drying.

$^1$H NMR (D$_2$O, 300 MHz): δ 3.06 (d, 2H), 3.86 (m, 2H), 4.39 (m, 1H), 4.91 (m, 1H), 5.18 (m, 1H), 5.36 (t, 1H), 5.63 (d, 1H), 7.23 (m, 5H), 8.09 (s, 1H), 8.20 (s, 1H). $^{31}$P NMR (D$_2$O, 121.47 MHz): δ 2.17 (s).

Example 15

2',3'-cinnamyl acetal adenosine 5'-monophosphate

Adenosine 5'-monophosphate, free acid (1.0 g, 2.88 mmol) was dissolved in 98% formic acid (5 mL) and cinnamaldehyde (1.14 g, 8.65 mmol) added. The reaction was stirred at ambient temperature for 3 hours, after which the formic acid was evaporated and the residue partitioned between 1 M sodium bicarbonate (25 mL) and ethyl acetate (20 mL). The layers were separated, and the product was isolated from the aqueous layer via preparative HPLC. Yield=0.202 g (15%).

$^1$H NMR (D20, 300 MHz): δ 3.97 (m, 2H), 4.50 (m, 1H), 5.04 (m, 1H), 5.29 (m, 1H), 5.65 (d, 0.4H), 5.86 (d, 0.6H), 6.24 (m, 2H), 6.87 (dd, 1H), 7.27 (m, 3H), 7.43 (m, 2H), 8.12 (d, 1H), 8.28 (d, 1H). $^{31}$P NMR (D$_2$O, 121.47 MHz): δ 1.42 (d).

Example 16

2',3'-phenylacetaldehyde acetal-6-N-phenylurea adenosine 5'-monophosphate (compound 22)

2',3'-phenylacetaldehyde acetal adenosine 5'-monophosphate, tributylammonium salt (prepared according to example 14, 1.0 g, 2.15 mmol) was dissolved in N,N-dimethylformamide (10 mL) and phenylisocyanate (1.17 g, 10.72 mmol) added. The reaction was heated at 35° C. for 4 hrs, after which the solvent was removed and the residue partitioned between 1 M sodium bicarbonate (30 mL) and ethyl acetate (25 mL). The layers were separated and the product isolated from the aqueous layer via preparative HPLC. Yield=0.85 g (68%).

$^1$H NMR (D$_2$O, 300 MHz): δ 2.97 (d, 2H), 3.81 (m, 2H), 4.31 (m, 1H), 4.78 (m, 1H), 4.98 (m, 1H), 5.23 (t, 1H), 5.63 (d, 1H), 6.74 (m, 1H), 6.96 (m, 4H), 7.19 (m, 5), 8.12 (s, 1H), 8.30 (s, 1H). $^{31}$P NMR (D$_2$O, 121.47 MHz): δ 1.19 (s).

Example 17

2',3'-cinnamyl acetal-6N-ethylurea adenosine 5'-monophosphate (compound 27)

Compound 27 was prepared according to example 16, starting with 2'3' cinnamyl acetal adenosine 5'-monophosphate (example 15) and substituting ethyl isocyanate for phenylisocyanate. Yield=65%.

1H NMR (D$_2$O, 300 MHz): δ 1.07 (t, 3H), 3.21 (q, 2H), 3.93 (m, 2H), 4.45 (m 4.99 (m, 1H), 5.28 (m, 1H), 5.54 (d, 0.3H), 5.70 (d, 0.7H), 5.95 (m, 1H), 6.14 (m, 1H), 6.61 (dd, 1H), 7.14 (m, 5H), 8.29 (m, 2H). $^{31}$P NMR (D$_2$O, 121.47 MHz): δ 1.93 (d).

Example 18

Inhibition of ADP-Induced Platelet Aggregation

Isolation of platelets: Human blood was obtained from informed healthy volunteers. Blood was collected into one-sixth volume of ACD (2.5 g of sodium citrate, 1.5 g citric acid, and 2.5 g glucose in 100 ml dH$_2$O). Blood was centrifuged at 800×g for 15 min at room temperature and the platelet-rich plasma removed and incubated for 60 min at 37° C. in the presence of 1 mM acetylsalicylic acid followed by centrifugation at 1000×g for 10 min at room temperature. The platelet pellet was resuspended at a density of 2×1 8 cells/ml with HEPES-buffered Tyrode's solution (137 mM NaCl, 2.7 mM KCl, 1 mM MgCl$_2$, 3 mM NaH$_2$PO$_4$, 5 mM glucose, 10 mM HEPES pH 7.4, 0.2% bovine serum albumin, and 0.05 U/ml apyrase).

Aggregation Studies: ADP-induced platelet aggregation was determined by measuring the transmission of light through a 0.5 ml suspension of stirred (900 rpm) aspirin-treated washed platelets in a lumi-aggregometer at 37° C. (Chrono-Log Corp. Havertown, Pa.). The baseline of the instrument was set using 0.5 ml of Hepes-buffered Tyrode's solution. Prior to aggregation measurements, the platelet suspension was supplemented with 2 mM CaCl$_2$ and 1 mg/ml fibrinogen. Platelet aggregation was initiated by the addition of indicated concentrations of ADP or other agonists, and the light transmission continuously recorded for at least 8 min. When inhibitors of platelet aggregation were tested, platelets were incubated for 3–6 min in the presence of indicated concentrations of inhibitor before addition of ADP or other agonists, and the response recorded for at least 8 min. The potency of agonists and inhibitors of platelet aggregation was calculated from both, the rate of aggregation and the maximal extent of aggregation obtained for each determination by fitting the data to a four-parameter logistic equation using the GraphPad software package (GraphPad Corp. San Diego, Calif.).

The ability of P2Y$_{12}$ antagonists to inhibit platelet aggregation is presented in this application as the percent inhibition of the aggregation induced by a maximally effective concentration of ADP. When a broad range of concentrations of P2Yl$_2$ antagonist was tested (usually from 1 nM to 100 μM), an IC$_{50}$ value was also obtained. IC$_{50}$ values represent the concentration of antagonist needed to inhibit by 50% the aggregation elicited by a given concentration of ADP.

Example 19

Effects on Platelet Aggregation In Vivo

To evaluate the ability of these compounds to inhibit platelet aggregation in vivo, an experimental protocol similar to the method of R. G. Humphries et al. (Br. J. Pharmacol. 115:1110–1116, 1995) will be performed.

Surgical Preparation and Instrumentation: Male Sprague-Dawley rats are anesthetized. Body temperature is maintained at 37±0.5° C. with a heating lamp. Animals breathe spontaneously and a tracheotomy is performed to ensure a patent airway. A cannula containing heparinized saline is introduced into the left femoral artery and connected to a transducer to record blood pressure and heart rate. Cannulae containing non-heparinized saline are introduced into the left common carotid artery and left jugular vein for withdrawal of arterial blood samples and i.v. administration of compounds, respectively. Experimental Protocol: Either compound or vehicle is administered to each animal as an infusion. Blood samples are taken immediately prior to the first infusion, at the end of each infusion and 20 min after cessation of the final infusion for measurement of platelet aggregation ex vivo. Immediately after sampling, ADP-induced platelet aggregation is measured in duplicate in 0.5 ml blood samples diluted 1:1 with saline and incubated at 37° C. for 4 min. For the final minute of this period, cuvettes are transferred to a lumi-aggregometer and the sample stirred at 900 rpm. ADP (3 µM) is added in a volume of 20 µl and the aggregation response is recorded.

Example 20

Inhibition of Thrombus Formation in Anesthetized Rats

To evaluate the effect of these compounds on thrombus formation in vivo, the following experimental protocol will be performed.

Rats (CD-1; male; approximately 350 grams; Charles River, Raleigh, N.C.), are anesthetized with sodium pentobarbital (70 mg/kg i.p.). The abdomens are shaved and a 22 gauge intravenous catheter is inserted into a lateral tail vein. A midline incision is made and the intestines are wrapped in saline-soaked gauze and positioned so the abdominal aorta is accessible. The inferior vena cava and abdominal aorta are carefully isolated and a section (approx. 1 cm) of the abdominal aorta (distal to the renal arteries proximal to the bifurcation) is dissected. All branches from the aorta in this section are ligated with 4–0 silk suture. A 2.5 mm diameter flow probe connected to a Transonic flow meter is placed on the artery and a baseline (pre-stenosis) flow is recorded. Two clips are placed around the artery decreasing the vessel diameter by approximately 80%. A second baseline flow measurement is taken (post-stenosis) and the hyperemic response is tested. Animals are then treated with either compound or saline i.v., via tail vein catheter. Thrombosis is induced five minutes after treatment by repeated external compressions of the vessel with hemostatic forceps. Two minutes post-injury, the vessel compressions are repeated and a 10 minute period of flow monitoring is started. Animals are monitored continuously for a minimum of the first ten minutes post-injury. After twenty minutes (post-injury), a flow measurement is repeated and the animals are euthanized. The section of the aorta that includes the injured section is harvested and placed in 10% formalin for possible histologic evaluation.

Example 21

Inhibition of Thrombus Formation in Anesthetized Dogs

To evaluate the effect of these compounds on dynamic thrombus formation in vivo, the following experimental protocol similar to the method of J. L. Romson et al. (*Thromb. Res.* 17:841–853, 1980) will be performed.

Surgical Preparation and Instrumentation: Briefly, purpose-bred dogs are anesthetized, intubated and ventilated with room air. The heart is exposed by a left thoracotomy in the fifth intercostal space and suspended in a pericardial cradle. A 2–3 cm segment of the left circumflex coronary artery (LCCA) is isolated by blunt dissection. The artery is instrumented from proximal to distal with a flow probe, a stimulation electrode, and a Goldblatt clamp. The flow probe monitors the mean and phasic LCCA blood flow velocities. The stimulation electrode and its placement in the LCCA and the methodology to induce an occlusive coronary thrombus have been described previously (J. K. Mickelson et al., *Circulation* 81:617–627, 1990; R. J. Shebuski et al., *Circulation* 82:169–177, 1990; J. F. Tschopp et al., *Coron. Artery Dis.* 4:809–817, 1993).

Experimental Protocol: Dogs are randomized to one of four treatment protocols (n=6 per treatment group) in which the control group receives saline i.v. and the three drug-treated groups are administered compound i.v. Upon stabilization from the surgical interventions, dogs receive either saline or compound. After approximately 30 minutes, an anodal current is applied to the LCCA for 180 min. The number and frequency of cyclic flow variations (CFV) that precede formation of an occlusive thrombus are recorded. These cyclic phenomena are caused by platelet thrombi that form in the narrowed lumen as a result of platelet aggregation (J. D. Folts et al., *Circulation* 54:365–370, 1976; Bush et al., Circulation 69:1161–1170, 1984). Zero flow in the LCCA for a minimum of 30 minutes indicates a lack of antithrombotic efficacy (L. G. Frederick et al., *Circulation* 93:129–134, 1996).

Example 22

ADP-Induced Aggregation by Different Compounds

Different compounds were tested for their inhibition of ADP-induced aggregation and their $IC_{50}$ according to the protocols in Example 18; the results are shown in FIG. 1. The bar graphs in the figure illustrate the effect of 100 µM concentration of the compound on ADP-induced platelet aggregation, and the data are expressed as % inhibition of the ADP response.

FIG. 1 shows the structure and abbreviated name of each compound and its activity. Where hydrogens are understood to be present, they have been omitted for the sake of simplicity. For example, for the first structure of the figure, it is implied that there are hydrogens at the 3-position of the pyrimidine ring, at the 3'-position of the ribose on the oxygen, and on the nitrogen of the carbamate at the 2'-position of the ribose. In addition, as disclosed within the scope of the present invention, it is implied that the oxygens that are not doubly bonded to the phosphorous atoms are either present in the ionized form as salts with a counterion, or are bonded to a hydrogen atom. For simplicity, some of the structures in the figure are portrayed in the salt form, but this should not be interpreted as excluding the possibility that hydrogens could be present instead.

Several parent compounds, Up4U, Ip4U, Up3U, and Cp4U, without modifications on the furanose hydroxyl groups, have been included at the end of the figure to illustrate the utility of the present invention. However, these unmodified parent compounds do not inhibit the ADP-induced aggregation and are not within the scope of the present invention.

Although the invention has been described with reference to the presently preferred embodiments, it should be understood that various modifications could be made without departing from the scope of the invention.

What is claimed:
1. A compound of Formula Ib' or salts thereof:

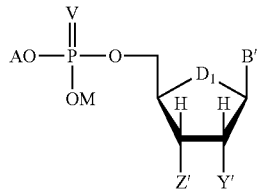

Formula Ib' wherein:
V=O;
A=M;
M=H or a pharmaceutically-acceptable inorganic or organic counterion;
$D_1$=O;
Y'=$OR_1$;
Z'=$OR_2$;
$R_1$ and $R_2$ are residues which are linked directly to two of the 2' and 3' hydroxyls of the furanose via a common carbon atom according to Formula III,

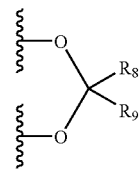

Formula III wherein:
O is the 2' and 3' oxygens of the furanose; and
the 2' and 3' oxygens of the furanose are linked by a common carbon atom to form a cyclical acetal; and
$R_8$ is hydrogen; and
$R_9$ is selected from the group consisting of aralkyl, aryl, substituted aralkyl, and substituted aryl;
in which the aralkyl groups are straight chained from 1 to 5 carbons, with or without unsaturation and without heteroatoms in the alkyl portion, and are monocyclic moieties from 5 to 6 carbons in the aryl portion; and in which the aryl groups are monocyclic moieties from 4 to 6 carbons, with or without heteroatoms;
B' is a purine residue according to general Formula IV:

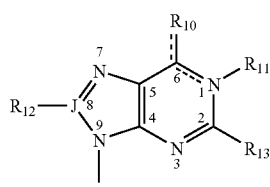

Formula IV wherein J=carbon;
$R_{11}$ is absent;
$R_{12}$ is hydrogen;
$R_{13}$ is hydrogen;
$R_{10}$ is acylamino, according to Formula VI;

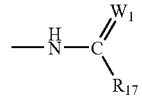

Formula VI wherein:
NH is the amino residue at the C-6 position in a purine;
C is a carbon atom;
$W_1$ is oxygen; and
$R_{17}$ is amino or mono- or disubstituted amino such that the moiety according to Formula VI is a urea.

2. The compound according to claim 1, wherein $R_9$ is selected from the group consisting of aralkyl, aryl, substituted aralkyl, and substituted aryl; in which the aralkyl groups are straight chained from 3 to 4 carbons, with or without unsaturation and without heteroatoms in the alkyl portion, and are monocyclic moieties of 6 carbons without heteroatoms in the aryl portion; and the aryl groups are monocyclic moieties of 6 carbons, without heteroatoms.

3. A compound selected from the group consisting of: 2'3' phenylacetaldehyde acetal-6-N-phenylurea AMP; 2'3' phenylacetaldehyde acetal-6-N-n-hexylurea AMP; 2'3' phenylacetaldehyde acetal-6-N-ethylurea AMP; 2'3' phenylacetaldehyde acetal-6-N-cyclopentylurea AMP; 2'3' cinnamyl acetal-6-N-n-hexylurea AMP; 2'3' cinnamyl acetal-6-N-ethylurea AMP; 2'3' cinnamyl acetal-6-N-phenylurea AMP; 2'3' cinnamyl acetal-6-N-n-propylurea AMP; 2'3' cinnamyl acetal-6-N-n-butylurea AMP; 2'3' phenylpropargyl acetal-6-N-phenylurea AMP; 2'3' phenylpropargyl acetal-6-N-n-hexylurea AMP; 2'3' phenylpropargyl acetal-6-N-n-butylurea AMP; 2'3' phenylpropargyl acetal-6-N-n-propylurea AMP; 2'3' phenylpropargyl acetal-6-N-ethylurea AMP; 2'3' benzaldehyde acetal-6-N-ethylurea AMP; 2'3' benzaldehyde acetal-6-N-n-propylurea AMP; 2'3' benzaldehyde acetal-6-N-n-butylurea AMP; 2'3' benzaldehyde acetal-6-N-n-hexylurea AMP; and 2'3' benzaldehyde acetal-6-N-cyclopentylurea AMP, or salts thereof.

4. A pharmaceutical formulation comprising the compound according to claim 1 and a pharmaceutically acceptable carrier.

5. A pharmaceutical formulation comprising the compound according to claim 3 and a pharmaceutically acceptable carrier.

6. A method of treating diseases or conditions associated with platelet aggregation comprising:
administering to a subject the pharmaceutical formulation according to claim 4, wherein said compound is effective to bind $P2Y_{12}$ receptors on platelets and inhibit ADP-induced platelet aggregation.

7. A method of treating diseases or conditions associated with platelet aggregation comprising:
administering to a subject the pharmaceutical formulation according to claim 5, wherein said compound is effective to bind $P2Y_{12}$ receptors on platelets and inhibit ADP-induced platelet aggregation.

8. The method according to claim 6, wherein said pharmaceutical composition reduces the incidence of dose-related adverse side effects of other therapeutic agents that are used to prevent, manage or treat platelet aggregation disorders.

9. The method according to claim 6, wherein said diseases or conditions associated with platelet aggregation are disorders or procedures characterized by thrombosis, primary arterial thrombotic complications of atherosclerotic disease, thrombotic complications of interventions of atherosclerotic disease, thrombotic complications of surgical or mechanical damage, mechanically-induced platelet activation, shunt occlusion, thrombosis secondary to vascular damage and inflammation, indications with a diffuse thrombotic/platelet consumption component, venous thrombosis, coronary arterial thrombosis, pathological effects of atherosclerosis and arteriosclerosis, platelet aggregation and clot formation in blood and blood products during storage, chronic or acute states of hyper-aggregability, reocclusion of an artery or vein following fibrinolytic therapy, platelet adhesion associated with extracorporeal circulation, thrombotic complications associated with thrombolytic therapy, thrombotic complications associated with coronary and other angioplasty, or thrombotic complications associated with coronary artery bypass procedures.

10. The method according to claim 9, wherein said disorders or procedures associated with thrombosis are unstable angina, coronary angioplasty, or myocardial infarction; said primary arterial thrombotic complications of atherosclerosis are thrombotic stroke, peripheral vascular disease, or myocardial infarction without thrombolysis; said thrombotic complications of interventions of atherosclerotic disease are angioplasty, endarterectomy, stent placement, coronary or other vascular graft surgery; said thrombotic complications of surgical or mechanical damage are associated with tissue salvage following surgical or accidental trauma, reconstructive surgery including skin flaps, or reductive surgery; said mechanically-induced platelet activation is caused by cardiopulmonary bypass resulting in microthromboembolism and storage of blood products; said shunt occlusion is renal dialysis and plasmapheresis; said thromboses secondary to vascular damage and inflammation are vasculitis, arteritis, glomerulonephritis or organ graft rejection; said indications with a diffuse thrombotic/platelet consumption component are disseminated intravascular coagulation, thrombotic thrombocytopenic purpura, hemolytic uremic syndrome, heparin-induced thrombocytopenia, or pre-eclampsia/eclampsia; said venous thrombosis are deep vein thrombosis, veno-occlusive disease, hematological conditions, or migraine; and said coronary arterial thrombosis is associated with unstable angina, coronary angioplasty or acute myocardial infarction.

11. The method according to claim 10, wherein said hematological conditions are thrombocythemia or polycythemia.

12. The method according to claim 9, wherein said pathological effects of atherosclerosis and arteriosclerosis are arteriosclerosis, acute myocardial infarction, chronic stable angina, unstable angina, transient ischemic attacks, strokes, peripheral vascular disease, arterial thrombosis, pre-eclampsia, embolism, restenosis or abrupt closure following angioplasty, carotid endarterectomy, or anastomosis of vascular grafts; said chronic or acute states of hyper-aggregability is caused by DIC, septicemia, surgical or infectious shock, post-operative trauma, post-partum trauma, cardiopulmonary bypass surgery, incompatible blood transfusion, abruptio placenta, thrombotic thrombocytopenic purpura, snake venom or immune diseases.

13. The method according to claim 9, wherein said reocclusion of an artery or vein following fibrinolytic therapy is inhibited by internal administration of said compound with a fibrinolytic agent.

14. The method according to claim 13, wherein said fibrinolytic agent is a natural or synthetic product which directly or indirectly causes lysis of a fibrin clot.

15. The method according to claim 13, wherein said fibrinolytic agent is a plasminogen activator selected from the group consisting of anistreplase, urokinase, pro-urokinase, streptokinase, tissue plasminogen activator and mutants, or variants thereof, which retain plasminogen activator activity.

16. The method according to claim 15, wherein said variants are selected from the group consisting of variants which have been chemically modified, variants which one or more amino acids have been added, deleted or substituted, and variants with one or more modified functional domains.

17. The method according to claim 16, wherein said modified functional domains are added, deleted or altered by combining the active site of one plasminogen activator or fibrin binding domain of another plasminogen activator or fibrin binding molecule.

18. The method according to claim 6, wherein said administering is systemic administration of said compound to a subject.

19. The method according to claim 18, wherein said systemic administration is an administration selected from the group consisting of: injecting an injectable form of said compound; administering by mouth an oral form of said compound; applying to the skin a transdermal patch or a transdermal pad containing said compound; administering a liquid/liquid suspension of said compound via nose drops or nasal spray; administering a nebulized liquid of said compound to oral or nasopharyngeal airways; administering rectally a suppository form of said compound; administering vaginally said compound in dosage unit formulations containing conventional non-toxic pharmaceutically acceptable carriers, adjuvants and vehicles; administering said compound intravitreally; and administering via intra-operative instillation a gel, cream, powder, foam, crystals, liposomes, spray or liquid suspension form of said compound; such that a therapeutically effective amount of said compound contacts the target platelets of said patient via systemic absorption and circulation.

20. The method according to claim 18, wherein said systemic administration comprises infusion of said compound to target platelets via a device selected from the group consisting of a pump catheter system and a continuous or selective release device.

21. The compound according to claim 1, wherein $R_9$ is aralkyl, in which the alkyl portion is a 2-carbon chain with unsaturation, and the aryl portion is a phenyl ring.

22. A pharmaceutical formulation comprising the compound according to claim 21 and a pharmaceutically acceptable carrier.

23. A compound of Formula Ib" or salts thereof:

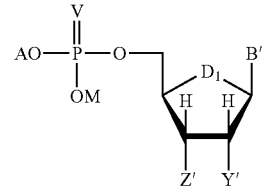

Formula Ib"

wherein:
V═O;
A═M;
M═H or a pharmaceutically-acceptable inorganic or organic counterion;

$D_1 = O$;
Y'=H, OH, or $OR_1$;
Z'=H, OH, or $OR_2$; with the proviso that at least one of Y" and Z' is $OR_1$ or $OR_2$;
$R_1$ and $R_2$ are residues which are linked directly to the 2' and /or 3' hydroxyls of the furanose via a carbon atom according to Formula II,

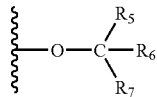

Formula II wherein:
O is the corresponding 2'- and/or 3'-oxygen of the respective furanose or carbocycle;
C is a carbon atom;
$R_5$, $R_6$, and $R_7$ are H, alkyl, cycloalkyl, aralkyl, aryl, substituted aralkyl, or substituted aryl, such that the moiety defined according to Formula II is an ether; or
$R_5$ and $R_6$ are H, an alkyl, cycloalkyl, aralkyl, aryl, substituted aralkyl, or substituted aryl, and $R_7$ is alkoxy, cycloalkoxy, aralkyloxy, aryloxy, substituted aralkyloxy, or substituted aryloxy such that the moiety defined according to Formula II is an acyclic acetal or ketal; or
$R_5$ and $R_6$ are taken together as oxygen or sulfur doubly bonded to C, and $R_7$ is alkyl, cycloalkyl, aralkyl, aryl, substituted aralkyl, or substituted aryl, such that the moiety defined according to Formula II is an ester or thioester; or
$R_5$ and $R_6$ are taken together as oxygen or sulfur doubly bonded to C, and $R_7$ is amino or mono- or disubstituted amino, where the substituents are alkyl, cycloalkyl, aralkyl, aryl, substituted aralkyl, or substituted aryl, such that the moiety according to Formula II is a carbamate or thiocarbamate; or
$R_5$ and $R_6$ are taken together as oxygen or sulfur doubly bonded to C, and $R_7$ is alkoxy, cycloalkoxy, aralkyloxy, aryloxy, substituted aralkyloxy, or substituted aryloxy, such that the moiety according to Formula II is a carbonate or thiocarbonate; or
$R_7$ is not present and $R_5$ and $R_6$ are taken together as oxygen or sulfur doubly bonded to C and both the 2'- and 3'-oxygens of the respective furanose or carbocycle are directly bound to C to form a cyclical carbonate or thiocarbonate;
B' is a purine residue according to general Formula IV:

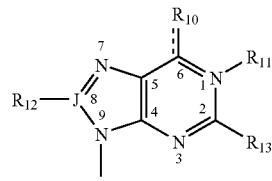

Formula IV wherein J=carbon;
$R_{11}$ is absent;
$R_{12}$ is hydrogen;
$R_{13}$ is hydrogen;
$R_{10}$ is acylamino, according to Formula VI;

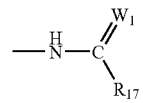

Formula VI wherein:
NH is the amino residue at the C-6 position in a purine;
C is a carbon atom;
$W_1$ is oxygen; and
$R_{17}$ is amino or mono- or disubstituted amino such that the moiety according to Formula VI is a urea.

24. The compound according to claim 3, wherein said compound is 2'3' cinnamyl acetal-6-N-ethylurea AMP or salts thereof.

25. The method according to claim 6, wherein said compound is 2'3' cinnamyl acetal-6-N-ethylurea AMP or salts thereof.

26. The method according to claim 7, wherein said diseases or conditions associated with platelet aggregation are disorders or procedures characterized by thrombosis, primary arterial thrombotic complications of atherosclerotic disease, thrombotic complications of interventions of atherosclerotic disease, thrombotic complications of surgical or mechanical damage, mechanically-induced platelet activation, shunt occlusion, thrombosis secondary to vascular damage and inflammation, indications with a diffuse thrombotic/platelet consumption component, venous thrombosis, coronary arterial thrombosis, pathological effects of atherosclerosis and arteriosclerosis, platelet aggregation and clot formation in blood and blood products during storage, chronic or acute states of hyper-aggregability, reocclusion of an artery or vein following fibrinolytic therapy, platelet adhesion associated with extracorporeal circulation, thrombotic complications associated with thrombolytic therapy, thrombotic complications associated with coronary and other angioplasty, or thrombotic complications associated with coronary artery bypass procedures.

27. The method according to claim 26, wherein said disorders or procedures associated with thrombosis are unstable angina, coronary angioplasty, or myocardial infarction; said primary arterial thrombotic complications of atherosclerosis are thrombotic stroke, peripheral vascular disease, or myocardial infarction without thrombolysis; said thrombotic complications of interventions of atherosclerotic disease are angioplasty, endarterectomy, stent placement, coronary or other vascular graft surgery; said thrombotic complications of surgical or mechanical damage are associated with tissue salvage following surgical or accidental trauma, reconstructive surgery including skin flaps, or reductive surgery; said mechanically-induced platelet activation is caused by cardiopulmonary bypass resulting in microthromboembolism and storage of blood products; said shunt occlusion is renal dialysis and plasmapheresis; said thromboses secondary to vascular damage and inflammation are vasculitis, arteritis, glomerulonephritis or organ graft rejection; said indications with a diffuse thrombotic/platelet consumption component are disseminated intravascular coagulation, thrombotic thrombocytopenic purpura, hemolytic uremic syndrome, heparin-induced thrombocytopenia, or pre-eclampsia/eclampsia; said venous thrombosis are deep vein thrombosis, veno-occlusive disease, hematological conditions, or migraine; and said coronary arterial thrombosis is associated with unstable angina, coronary angioplasty or acute myocardial infarction.

* * * * *